(12) United States Patent
Smyth et al.

(10) Patent No.: US 12,038,433 B2
(45) Date of Patent: Jul. 16, 2024

(54) METHODS AND APPARATUS FOR HIGH-THROUGHPUT SCREENING FOR TESTING PERMEABILITY AND RETENTION OF COMPOUNDS ACROSS BIOLOGICAL BARRIERS

(71) Applicant: Board of Regents, The University of Texas System, Austin, TX (US)

(72) Inventors: Hugh Smyth, Austin, TX (US); Patricia Pereira Martins, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 601 days.

(21) Appl. No.: 17/015,293

(22) Filed: Sep. 9, 2020

(65) Prior Publication Data
US 2021/0072231 A1  Mar. 11, 2021

Related U.S. Application Data

(60) Provisional application No. 62/897,719, filed on Sep. 9, 2019.

(51) Int. Cl.
| | | |
|---|---|---|
| G01N 33/50 | (2006.01) | |
| A61K 35/36 | (2015.01) | |
| G01N 13/00 | (2006.01) | |
| G01N 13/04 | (2006.01) | |

(52) U.S. Cl.
CPC ......... *G01N 33/5082* (2013.01); *A61K 35/36* (2013.01); *G01N 13/00* (2013.01); *G01N 13/04* (2013.01); *G01N 33/5008* (2013.01)

(58) Field of Classification Search
CPC .... G01N 33/5082; G01N 13/00; G01N 13/04; G01N 33/5008; A61K 35/36
USPC .......................................................... 435/29
See application file for complete search history.

(56) References Cited

U.S. PATENT DOCUMENTS

| | | |
|---|---|---|
| 5,490,415 A | 2/1996 | Mak et al. |
| 6,043,027 A | 3/2000 | Selick et al. |
| 6,852,526 B2 * | 2/2005 | Cima et al. ............... C12M 1/34 |
| | | 435/288.4 |
| 7,022,528 B2 | 4/2006 | Avdeef et al. |

(Continued)

FOREIGN PATENT DOCUMENTS

| | | | | |
|---|---|---|---|---|
| JP | 2004504585 | * | 2/2004 | ......... G01N 33/5048 |
| WO | WO0071028 A1 | * | 5/2000 | ............... A61B 6/00 |
| WO | WO 02/06518 | | 1/2002 | |

OTHER PUBLICATIONS

Sjoval et al: Scientific Reports: Imaging the distribution of skin lipids and topically applied compounds in human skin using mass spectrometry. vol. 8, Article 16683, pp. 1-14 (Year: 2018).*

(Continued)

*Primary Examiner* — Jill A Warden
(74) *Attorney, Agent, or Firm* — Parker Highlander PLLC

(57) ABSTRACT

Devices, systems and methods to directly quantify molecular entities and, compounds, inactive ingredients, compositions or formulations across and into specific layers of biological membranes, such as the skin. Exemplary methods enable the determination of the amount of drug into and across tissues as well as the measurement of the effect of chemicals/compounds on membranes, mainly the skin.

9 Claims, 22 Drawing Sheets

(56) References Cited

U.S. PATENT DOCUMENTS

| | | | |
|---|---|---|---|
| 8,277,762 B2* | 10/2012 | Newsam et al. | B01L 3/00 |
| | | | 422/552 |
| 2004/0023841 A1 | 2/2004 | Mitragotri et al. | |
| 2005/0063862 A1* | 3/2005 | Roscoe | G01N 33/15 |
| | | | 422/68.1 |
| 2007/0183936 A1 | 8/2007 | Newsam et al. | |

OTHER PUBLICATIONS

Yang et al: Advanced Materials: Review, Drug Delivery: Getting Drugs Across Biological Barriers; vol. 29, Issue 37, p. 1-25 (Year: 2017).*
English translation of JP 2004504585 (Year: 2004).*
Franz et al., "Comparative Percutaneous Absorption", *Arch Dermatol*, 132:901-905, 1996.
Franz et al., "Percutaneous absorption. On the relevance of in vitro data", *Journal of Investigative Dermatology*, 64(3):190-195, 1975.
Franz et al., "The finite dose technique as a valid in vitro model for the study of percutaneous absorption in man", *InSkin-Drug Application and Evaluation of Environmental Hazards*, 7:58-68, 1978.
Karande et al., "Discovery of transdermal penetration enhancers by high-throughput screening", *Nature Biotechnology*, 22(2):192, 2004.
Karande et al., "High throughput screening of transdermal formational", *Pharmaceutical Research*, 19(5):655-660, 2002.
Karande et al., "Insights into synergistic interactions in binary mixtures of chemical permeation enhancers for transdermal drug delivery", *Journal of controlled release*, 115(1):85-93, 2006.
Sinkó et al., "Skin-PAMPA: A new method for fast prediction of skin penetration", *European Journal of Pharmaceutical Sciences*, 45(5):698-707, 2012.

* cited by examiner

Step 1:
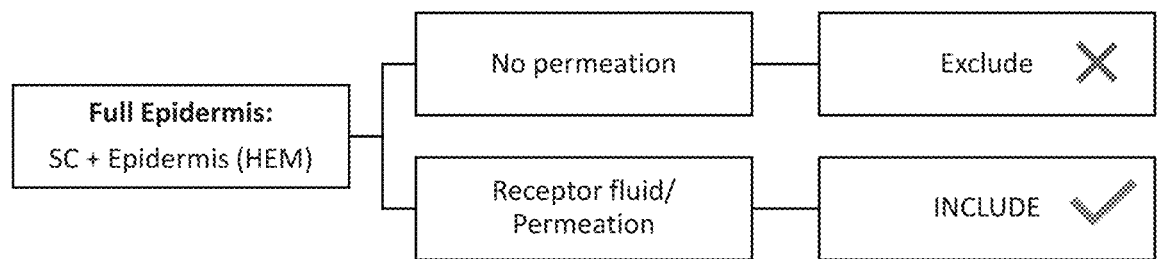
Step 2:
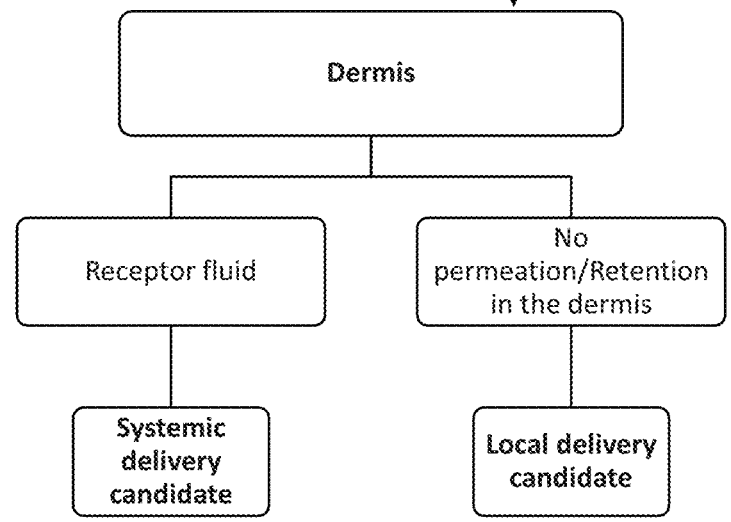
FIG. 14

| Solvent: Water | day 1 | day 2 (24 hours after) | day 3 (48 hours after) | 1 week notes |
|---|---|---|---|---|
| Crodamol SE 2% | clear solution | Haze on top. very small oil droplets form when shaken. | Haze on top. very small oil droplets form when shaken. | Haze on top. very small oil droplets form when shaken. |
| Crodamol SE 10% | clear solution | Haze on top. Small oil droplets form when shaken. | Haze on top. Small oil droplets form when shaken. | Haze on top. Small oil droplets form when shaken. |
| Crodamol IPM 2% | clear solution | Haze on top. very small oil droplets form when shaken. | Haze on top. very small oil droplets form when shaken. | Haze on top. very small oil droplets form when shaken. |
| Crodamol IPM 10% | clear solution | Haze on top. Small oil droplets form when shaken. | Haze on top. Small oil droplets form when shaken. | Haze on top. Small oil droplets form when shaken. |
| Dimethyl isosorbide 2% | clear solution | clear solution | clear solution | clear solution. slightly darker |
| Dimethyl isosorbide 10% | clear solution | clear solution | clear solution | clear solution. slightly darker |
| Super Refined Dimethyl Isorbide 2% | clear solution | clear solution | clear solution | clear solution. slightly darker |
| Super Refined Dimethyl Isorbide 10% | clear solution | clear solution | clear solution | clear solution. slightly darker |
| Transcutol 2% | clear solution | clear solution | clear solution | clear solution. slightly darker |
| Transcutol 10% | clear solution | clear solution | clear solution | clear solution. slightly darker |
| Oleic acid 2% | clear solution | Haze on top. very small oil droplets form when shaken. | Haze on top. very small oil droplets form when shaken. | Haze on top. very small oil droplets form when shaken. |
| Oleic acid 10% | clear solution | Haze on top. Small oil droplets form when shaken. | Haze on top. Small oil droplets form when shaken. | Haze on top. Small oil droplets form when shaken. |
| Isostearic acid 2% | clear solution | Haze on top. very small oil droplets form when shaken. | Haze on top. very small oil droplets form when shaken. | Haze on top. very small oil droplets form when shaken. |
| Isostearic acid 10% | clear solution | Haze on top. Small oil droplets form when shaken. | Haze on top. Small oil droplets form when shaken. | Haze on top. Small oil droplets form when shaken. |
| Tween 80 2% | clear solution | clear solution | clear solution | clear solution. slightly darker |
| Tween 80 10% | clear solution | clear solution | clear solution | clear solution. slightly darker |

FIG. 15

| | | | | |
|---|---|---|---|---|
| Tween 60 2% | clear solution | Tween solidified in solution. | Tween solidified in solution. | Tween solidified in solution. |
| Tween 60 10% | clear solution | Tween solidified in solution. | Tween solidified in solution. | Tween solidified in solution. |
| Tween 40 2% | clear solution | clear solution | clear solution | clear solution. slightly darker |
| Tween 40 3% | clear solution | clear solution | clear solution | clear solution. slightly darker |
| Tween 20 2% | clear solution | clear solution | clear solution | clear solution. slightly darker |
| Tween 20 10% | clear solution | clear solution | clear solution | clear solution. slightly darker |
| Span 20 2% | Cloudy but homogeneous | Cloudy but homogeneous | Cloudy but homogeneous | |
| Span 20 5% | Cloudy but homogeneous | Cloudy but homogeneous | Cloudy but homogeneous | |
| Span 40 2% | | | | |
| Span 60 2% | Couldnt get excipient into aqueous phase | Couldnt get excipient into aqueous phase | Couldnt get excipient into aqueous phase | Couldnt get excipient into aqueous phase |
| Span 60 5% | Couldnt get excipient into aqueous phase | Couldnt get excipient into aqueous phase | Couldnt get excipient into aqueous phase | Couldnt get excipient into aqueous phase |
| Span 80 2% | Cloudy but homogeneous | Cloudy but homogeneous | Cloudy but homogeneous | |
| Span 80 5% | Cloudy but homogeneous | Cloudy but homogeneous | Cloudy but homogeneous | |
| Span 83 2% | Cloudy but homogeneous | *Separated. Homogeneous when shaken.* | Separated. Homogeneous when shaken. | Separated. Homogeneous when shaken. |
| Span 83 5% | Cloudy but homogeneous | *Separated. Homogeneous when shaken.* | Separated. Homogeneous when shaken. | Separated. Homogeneous when shaken. |
| Poloxamer 237 0.1% | clear solution | clear solution | clear solution | clear solution |
| Poloxamer 237 2% | clear solution | clear solution | clear solution | clear solution |
| Poloxamer 124 0.1% | clear solution | clear solution | clear solution | clear solution |
| Poloxamer 124 2% | clear solution | clear solution | clear solution | clear solution |
| Poloxamer 407 0.1% | clear solution | clear solution | clear solution | clear solution |

FIG. 15 cont.

| | | | | |
|---|---|---|---|---|
| Poloxamer 407 2% | clear solution | clear solution | clear solution | clear solution |
| Poloxamer 181 0.1% | clear solution | clear solution | clear solution | clear solution |
| Poloxamer 181 2% | clear solution | clear solution | clear solution | clear solution |
| Poloxamer 182 0.1% | clear solution | clear solution | clear solution | clear solution |
| Poloxamer 182 2% | clear solution | clear solution | clear solution | clear solution |
| Poloxamer 188 0.1% | clear solution | clear solution | clear solution | clear solution |
| Poloxamer 188 2% | clear solution | clear solution | clear solution | clear solution |
| PEG 8 stearate 2% | Excipient solidified. | Excipient solidified. | Excipient solidified. | Excipient solidified. |
| PEG 8 stearate 5% | Excipient solidified. | Excipient solidified. | Excipient solidified. | Excipient solidified. |
| PEG 100 stearate 2% | clear solution | clear solution | clear solution | clear solution |
| Polyoxyl 40 stearate 2% | clear solution | clear solution | clear solution | clear solution, slightly darker |
| Polyoxyl 40 stearate 5% | clear solution | clear solution | clear solution | clear solution, slightly darker |
| Oleth-5 2% | Cloudy but homogeneous | Cloudy but homogeneous | Cloudy but homogeneous | Cloudy but homogeneous |
| Oleth-10 2% | clear solution | clear solution | clear solution | clear solution, slightly darker |
| Ceteth-20 2% | clear solution | clear solution | clear solution | clear solution |
| Ceteth-20 10% | clear solution/very slightly cloudy | clear solution | clear solution | clear solution |
| Laureth-4 2% | Cloudy but homogeneous | Cloudy but homogeneous | Cloudy but homogeneous | Cloudy but homogeneous |
| Laureth-4 5% | Cloudy but homogeneous | Cloudy but homogeneous | Cloudy but homogeneous | Cloudy but homogeneous |
| Laureth-23 0.45% | clear solution | clear solution | clear solution | clear solution, slightly darker |
| Laureth-23 2% | clear solution | clear solution | clear solution | clear solution, slightly darker |

FIG. 15 cont.

| Solvent: PG | day 1 | day 2 | day 3 | 1 week notes |
|---|---|---|---|---|
| Crodamol SE 2% | | | | |
| Crodamol SE 10% | | | | |
| Crodamol IPM 2% | | | | |
| Crodamol IPM 10% | | | | |
| Dimethyl isosorbide 2% | | | | |
| Dimethyl isosorbide 10% | | | | |
| Super Refined Dimethyl Isorbide 2% | | | | |
| Super Refined Dimethyl Isorbide 10% | | | | |
| Transcutol 2% | | | | |
| Transcutol 10% | | | | |
| Oleic acid 2% | | | | |
| Oleic acid 10% | | | | |
| Isostearic acid 2% | clear solution | clear solution | clear solution | clear solution |
| Isostearic acid 10% | clear solution | clear solution | clear solution | clear solution |
| Tween 80 2% | Cloudy but homogeneous | Cloudy but homogeneous | Cloudy but homogeneous | Cloudy but homogeneous |
| Tween 80 10% | Cloudy but homogeneous | Cloudy but homogeneous | Cloudy but homogeneous | It was slightly cloudy had small oil droplets but once shaken got cloud and homogeneous |
| Tween 60 2% | Cloudy but homogeneous | Cloudy but homogeneous | Cloudy but homogeneous | Cloudy but homogeneous |

FIG. 15 cont.

| | | | | |
|---|---|---|---|---|
| Tween 60 10% | Cloudy but homogeneous | It gelled or turned more viscous but still homogeneous | gelly and viscous as in Day 2 | Cloudy but homogeneous. Not gelly anymore or as viscous as 2% |
| Tween 40 2% | Cloudy but homogeneous | Cloudy but homogeneous | Cloudy but homogeneous | Cloudy but homogeneous |
| Tween 40 3% | Cloudy but homogeneous | Cloudy but homogeneous | Cloudy but homogeneous | Cloudy but homogeneous |
| Tween 20 2% | clear solution | clear solution | clear solution | clear solution |
| Tween 20 10% | Cloudy but homogeneous | Cloudy but homogeneous | Cloudy but homogeneous | Cloudy but homogeneous |
| Span 20 2% | Cloudy but homogeneous | Cloudy but homogeneous | Very small oil droplets on top. Redispersible when shaking | Very small oil droplets on top. Redispersible when shaking |
| Span 20 5% | Cloudy but homogeneous | Cloudy but homogeneous | Very small oil droplets on top. Redispersible when shaking | Very small oil droplets on top. Redispersible when shaking |
| Span 40 2% | At the beginning, right after shaking and heating it was cloudy but homogeneous. After 5 minutes it formed a white foam on top. Gets again homogeneous after mixing. | Cloud was present, non homogeneous becomes homogeneous but still cloudy after shaking | Separates white cloud on top and suspended particles all over. When mixed get cloudy but there seems to be suspended particles on it. | solid particles |
| Span 60 2% | Very hard to melt it. Once I stop heating it solidifies as small particles | opaque white cloud present, cloud disperses with shaking but white solids remain | opaque white cloud present, cloud disperses with shaking but white solids remain | solid particles |
| Span 60 5% | Very hard to melt it. Once I stop heating it solidifies as small particles | opaque white cloud present, cloud disperses with shaking but white solids remain | opaque white cloud present, cloud disperses with shaking but white solids remain | solid particles |
| Span 80 2% | Cloudy but homogeneous | Cloudy, a few oil droplets on top that are redispersed with mixing | Very small oil droplets on top. Redispersible when shaking | Very small oil droplets on top. Redispersible when shaking |

FIG. 15 cont.

| | | | | |
|---|---|---|---|---|
| Span 80 5% | Slightly Cloudy, small oily droplets on top even if mixing and sonicating | Cloudy with huge oil droplets on top. Maybe all the Span 80. Seems to be able to redisperse once shaking but rapiddly forms mini oil droplets on top after a few seconds to 1 minute | Big oil droplets on top. Redispersible when shaking | Big oil droplets on top. Redispersible when shaking |
| Span 83 2% | Cloudy but homogeneous | Cloudy but homogeneous | oilly droplets on surface, become homogeneous again after shaking | oilly droplets on surface, become homogeneous again after shaking |
| Span 83 5% | Big oil droplets on top. ONce mixing gets cloudy and homogeneous with no oil droplets. After less thana minute starts to form mini oil droplets | oilly droplets on surface, become homogeneous again after shaking | oilly droplets on surface, become homogeneous again after shaking | oilly droplets on surface, become homogeneous again after shaking |
| Poloxamer 237 0.1% | Clear solution | Excipient separates. Homogenous when shaken. | Excipient separates. Homogenous when shaken. | |
| Poloxamer 237 2% | Clear solution | Excipient separates. Not homogenous when shaken. | Excipient separates. Not homogenous when shaken. | |
| Poloxamer 124 0.1% | | | | |
| Poloxamer 124 2% | | | | |
| Poloxamer 407 0.1% | | cloudy but homogeneous | cloudy but homogeneous | cloudy but homogeneous |
| Poloxamer 407 2% | Clear solution but foamy on top with 3 solid particles? maybe didn't melt it enough | separated into two phases. several solid particles still present. Became homogeneous after shaking but particles were still present may need to repeat | 5 solidified flakes on top. white cake at the bottom. 2 phases. Did not work | 5 solidified flakes on top. white cake at the bottom. 2 phases. Did not work |
| Poloxamer 181 0.1% | | | | |
| Poloxamer 181 2% | | | | |
| Poloxamer 182 0.1% | | | | |

FIG. 15 cont.

| | | | | |
|---|---|---|---|---|
| Poloxamer 182 2% | | | | |
| Poloxamer 188 0.1% | | | Has white chunk on the bottom that is redispersible and gets cloudy and homogeneous. It almost seems like it was not melted enough or it partially solidified. I reheated it and got clear solution even after getting to room temperature. Will check again tomorrow | |
| Poloxamer 188 2% | | | Has white chunk on the bottom that is redispersible and gets cloudy and homogeneous. It almost seems like it was not melted enough or it partially solidified. I reheated it and got clear solution even after getting to room temperature. Will check again tomorrow | |
| PEG 8 stearate 2% | Cloudy but homogeneous | Cloudy but homogeneous | Has some small solidified particles. Maybe needed to heat properly. Heated but next day was cloudy and seemed like had some fine particles suspended | Has solidifed suspended particles |
| PEG 8 stearate 5% | Cloudy but homogeneous. There seems to be 2 very small waxy particles on top?Yes, and as it sits longer it forms more fine waxy particles | Big white chunks solidified | Big white chunks solidified | Big white chunks solidified |
| PEG 100 stearate 2% | | | | |
| Polyoxyl 40 stearate 2% | | cloudy but homogeneous | cloudy but homogeneous. Seems thicker | cloudy but homogeneous. Seems thicker |
| Polyoxyl 40 stearate 5% | | cloudy but homogeneous | cloudy but homogeneous. Seems thicker | cloudy but homogeneous. Seems thicker |
| Oleth-5 2% | | | | |
| Oleth-10 2% | | | | |
| Ceteth-20 2% | | slightly cloudy but homogeneous | slightly cloudy but homogeneous | slightly cloudy but homogeneous |

FIG. 15 cont.

| | very slightly cloudy but homogeneous | gelled, but looks good | gelled, but looks good | gelled, but looks good |
|---|---|---|---|---|
| Ceteth-20 10% | | | | |
| Laureth-4 2% | | | | |
| Laureth-4 5% | | | | |
| Laureth-23 0.45% | | | | |
| Laureth-23 2% | | | | |

| Solvent: Water:PG (50:50) | Initial | 24 hours | 48 hours |
|---|---|---|---|
| Crodamol SE 2% | cloudy but homogeneous | Small oil droplets form when shaking | Separated in 2 phases (SE on top). IT seems cloudy but homogeneous when shaking it. It seems to rapidly separate |
| Crodamol SE 10% | Cloudy and homogenous right after shaking it but after letting it sit for a few minutes seems to form 2 phases / a small white coud on top that redisperses after shaking | Separated in 2 phases (SE on top). IT seems cloudy but homogeneous when shaking it | Separated in 2 phases (SE on top). IT seems cloudy but homogeneous when shaking it but rapidly separates again |
| Crodamol IPM 2% | Slightly cloudy but homogeneous when shaken. When let it sit it seems clear | Slightly cloudy and homogeneous | Separated in 2 phases. IT seems cloudy but homogeneous when shaking it. It rapidly separates again |
| Crodamol IPM 10% | Cloudy and homogenous right after shaking it but seems to form oil droplets rapidly (seconds) after letting it sit and even forms 2 phases after a few minutes. It redisperses if shaking it | Had 2 phases (IPM on top). After shaking it it gets cloudy but homogeneous | Separated in 2 phases. IT seems cloudy but homogeneous when shaking it but rapidly separates again |
| Dimethyl isosorbide 2% | clear solution | clear solution | clear solution |
| Dimethyl isosorbide 10% | clear solution | clear solution | clear solution |
| Super Refined Dimethyl Isorbide 2% | clear solution | clear solution | clear solution |

FIG. 15 cont.

| | | | |
|---|---|---|---|
| Super Refined Dimethyl Isorbide 10% | clear solution | clear solution | clear solution |
| Transcutol 2% | clear solution | clear solution | clear solution |
| Transcutol 10% | clear solution | clear solution | clear solution |
| Oleic acid 2% | Cloudy and has oil droplets on top that remain after shaking | Cloudy and has oil droplets on top that remain after shaking | Cloudy and has oil droplets on top that remain after shaking |
| Oleic acid 10% | Cloudy and has oil droplets on top that remain after shaking | 2 phases, cloudy. Oil droplets on top that remain after shaking | 2 phases, cloudy. Oil droplets on top that remain after shaking |
| Isostearic acid 2% | Clear solution | Solution separated. Oil droplets on top when shaken. | Solution separated. Oil droplets on top when shaken. |
| Isostearic acid 10% | Clear solution | Solution separated. Oil droplets on top when shaken. | Solution separated. Oil droplets on top when shaken. |
| Tween 80 2% | Clear solution | Clear solution | Clear solution |
| Tween 80 10% | Clear solution | Clear solution | Clear solution |
| Tween 60 2% | Slightly cloudy but homogeneous | Cloudy with some haze flowing around. Not homogeneous. Some particles solidified | Cloudy with some haze flowing around. Not homogeneous. Some particles solidified |
| Tween 60 10% | Cloudy and has particles that solidified. Heated it and now is a clear solution. Look tomorrow | It is cloudy but homogeneous. No particles at all. (May need to repeat solution at 2% and heat it too) | there seems to be some haze at the bottom but after shaking it it seem good. no particles |
| Tween 40 2% | clear solution | clear solution | clear solution |
| Tween 40 3% | clear solution | clear solution | clear solution |
| Tween 20 2% | clear solution | clear solution | clear solution |
| Tween 20 10% | clear solution | clear solution | clear solution |
| Span 20 2% | cloudy but homgeneous | Separated in 2 phases. Oil on top but when shaken it gets homogenous and cloudy | Separated in 2 phases. Oil on top but when shaken it gets homogenous and cloudy |
| Span 20 5% | cloudy and seems to have Span 20 on top? IT redisperses once I shake | Separated in 2 phases. Oil on top but when shaken it gets homogenous and cloudy | Separated in 2 phases. Oil on top but when shaken it gets homogenous and cloudy |

FIG. 15 cont.

| | | | |
|---|---|---|---|
| Span 40 2% | It was cloudy and homogeneous but once let it sit some particles seem to be solified. | Solid particles floating. | Separation and Solid particles floating. |
| Span 60 2% | It was cloudy and homogeneous but once I let it sit it started froming a white cloud on top that redisperses after shaking | Solid particles all over | Separation and Solid particles all over |
| Span 60 5% | It was cloudy and homogeneous but once I let it sit it started froming a white cloud on top that redisperses after shaking | Solid particles all over | Separation and Solid particles all over |
| Span 80 2% | Cloudy and homogeneous once shaking. After letting it sit it forms oil droplets on top | Had oil droplets on top but once shaken it gets cloudy and homogeneous. Starts forming little oil droplets after 2 minutes | Had oil droplets on top but once shaken it gets cloudy and homogeneous. Starts forming little oil droplets after 2 minutes |
| Span 80 5% | Cloudy and homogeneous once shaking. After letting it sit it forms oil droplets on top. They even solidify | Had oil droplets on top but once shaken it gets cloudy and homogeneous. Starts forming little oil droplets after 2 minutes | Had oil droplets on top but once shaken it gets cloudy and homogeneous. Starts forming little oil droplets after 2 minutes |
| Span 83 2% | Cloudy and homogeneous but once we let it sit it forms oil droplets on top | Had oil droplets on top but once shaken it gets cloudy and homogeneous. Starts forming little oil droplets after 2 minutes | Had oil droplets on top but once shaken it gets cloudy and homogeneous. Starts forming little oil droplets after 2 minutes |
| Span 83 5% | Cloudy and homogeneous but once we let it sit it forms oil droplets on top | Had oil droplets on top but once shaken it gets cloudy and homogeneous. Starts forming little oil droplets after 2 minutes | Had oil droplets on top but once shaken it gets cloudy and homogeneous. Starts forming little oil droplets after 2 minutes |
| Poloxamer 237 0.1% | clear solution | clear solution | clear solution |
| Poloxamer 237 2% | clear solution | clear solution | clear solution |
| Poloxamer 124 0.1% | clear solution | clear solution | clear solution |
| Poloxamer 124 2% | clear solution | clear solution | clear solution |
| Poloxamer 407 0.1% | clear solution | clear solution | clear solution |
| Poloxamer 407 2% | clear solution | clear solution | clear solution (got slightly darker) |
| Poloxamer 181 0.1% | clear solution | clear solution | clear solution |

FIG. 15 cont.

| | | | |
|---|---|---|---|
| Poloxamer 181 2% | Cloudy but homogeneous | Cloudy but homogeneous | Cloudy but homogeneous |
| Poloxamer 182 0.1% | clear solution | clear solution | clear solution |
| Poloxamer 182 2% | clear solution | clear solution | clear solution |
| Poloxamer 188 0.1% | clear solution | clear solution | clear solution |
| Poloxamer 188 2% | clear solution | clear solution | clear solution |
| PEG 8 stearate 2% | seems to be starting to gel. Cloudy and homogenous | Completely gelled and seems homogeneous | Completely gelled and seems homogeneous |
| PEG 8 stearate 5% | completely gelled | completely gelled. It seems to have some whiter areas so not sure if it is just air or if it is good | completely gelled. It seems to have some whiter areas so not sure if it is just air or if it is good. It is good. when put on the vortex it looks good |
| PEG 100 stearate 2% | clear solution | clear solution | clear solution |
| Polyoxyl 40 stearate 2% | clear solution | clear solution | clear solution |
| Polyoxyl 40 stearate 5% | clear solution | clear solution | clear solution |
| Oleth-5 2% | very slightly cloudy and homogeneous | Light cloud on top that gets homogeneous after shaking it. Remains homogenous for more than 10 minutes | Light cloud on top that gets homogeneous after shaking it. Remains homogenous for more than 10 minutes |
| Oleth-10 2% | clear solution | clear solution | clear solution |
| Ceteth-20 2% | clear solution | clear solution | clear solution |
| Ceteth-20 10% | clear solution | clear solution | clear solution |
| Laureth-4 2% | clear solution | clear solution | clear solution |
| Laureth-4 5% | clear solution | clear solution | clear solution |
| Laureth-23 0.45% | clear solution | clear solution | clear solution |
| Laureth-23 2% | clear solution | clear solution | clear solution |

FIG. 15 cont.

METHODS AND APPARATUS FOR HIGH-THROUGHPUT SCREENING FOR TESTING PERMEABILITY AND RETENTION OF COMPOUNDS ACROSS BIOLOGICAL BARRIERS

CROSS-REFERENCE TO RELATED APPLICATIONS

This application claims priority to U.S. Provisional Patent Application Ser. No. 62/897,719 filed Sep. 9, 2019, the contents of which are incorporated by reference herein.

BACKGROUND INFORMATION

Embodiments of the present invention relate to methods and devices to directly quantify molecular entities and, compounds, inactive ingredients, compositions or formulations across and into specific layers of biological membranes, such as the skin. Those methods enable the determination of the amount of drug into and across tissues as well as the measurement of the effect of chemicals/compounds on membranes, mainly the skin.

Diffusion and permeation of substances across biological barriers is an important step in pharmacology and toxicology as it influences the amount of substances absorbed that can then exert either intended or unintended/unwanted effects. For example, in vitro skin permeation testing is needed for drug development of topical and transdermal formulations. For the last 40 years, diffusion cells, mainly Franz cells (FC) have been used as the gold-standard method to test the permeability of drugs/compounds and formulations across the skin or other membranes (1,2).

However, FC are limited by their low-throughput and requirement of high-quantities of tissue. For a FC with an area of diffusion of 0.64 $cm^2$, skin samples need to be cut to an area larger than the area of the diffusion of the Franz cell to be appropriately clamped in the system.

The Franz cells are composed by a receptor compartment and a donor compartment. The skin is clamped between the donor and receptor compartment. The donor compartment is used to place the drug/compound/formulation to be studied and it is in contact with the stratum corneum, the outermost layer of the skin. The dermis layer is in contact with the receptor compartment/receptor fluid. The amount of drug that permeated across the skin can be measured by taking aliquots from the receptor chamber and analyzing it using high performance liquid chromatography or any other method of analysis (1,2). Franz cells are currently commercialized by PermeGear (www.permegear.com) and Logan Instruments (http://www.loganinstruments.com).

Formulations tested using FC include but are not limited to topical, transdermal, ophthalmic, oral, cosmetics and personal care and consumer products, as well as pesticides.

A formulation can contain multiple ingredients, mainly in the case of topical formulations that are applied on the skin. It has previously been shown that the ingredients present in the formulation influence the permeability and retention of drugs in membranes being able to either enhance or retain compounds on the membrane. Based on the ingredients used, the formulations are optimized until the ideal permeability characteristics are obtained. From the formulations selected, at least 4 will need to be tested in vivo under Maximal Usage conditions to avoid any potentially harmful systemic side-effects. The selection of formulations to be included in the MUsT trials is based on IVPT. See e.g. https://www.fda.gov/media/125080/download. This means that multiple formulations are usually tested until the final product is developed.

Due to the low-throughput of the FC, high-throughput screening methods have previously been described. Karande and Mitragotri developed a method to help identify chemical penetration enhancers utilizing electric conductivity. Electrical conductivity is a measurement of the permeability of a membrane to ions and does not constitute a direct measurement of drugs inside or across the skin (3).

Another method currently available is the Skin-PAMPA which is currently commercialized by Pion Inc. PAMPA was first developed for the study of compounds across epithelial barriers such as the gastrointestinal barrier or even the blood-brain barrier (4,5). This method utilizes an artificial membrane and a modified microplate. For skin permeation purposes, the membrane is composed of only lipids that are part of the outermost layer of the skin which does not completely mimic the whole skin structure (4,5).

SUMMARY

Exemplary embodiments of the present disclosure include a method of analyzing membrane retention and permeation of compounds, where the method comprises securing a biological barrier between a first plurality of wells and a second plurality of wells; and contacting the biological barrier with a compound. In particular embodiments: the compound is initially contained in the first plurality of wells; the compound is in contact with the biological barrier for a period of time; and the compound comprises an analyte of interest. Specific embodiments include removing the biological barrier from between the first plurality of wells and the second plurality of wells; and analyzing the biological barrier to determine an amount of the analyte of interest retained in the biological barrier.

In certain embodiments, analyzing the biological barrier to determine the amount of the analyte of interest retained in the biological barrier comprises an optical/spectroscopical analysis of the biological barrier. In particular embodiments, the optical analysis comprises multi-photon microscopy. In specific embodiments, the optical analysis comprises two-photon microscopy. In some embodiments, the optical analysis comprises Raman spectroscopy.

In certain embodiments, the optical analysis comprises: directing an excitation light toward the biological barrier; and measuring an emitted light from the biological barrier. In particular embodiments, the emitted light is fluorescence emitted from the analyte of interest, and in specific embodiments the analyte of interest is a therapeutic compound.

In certain embodiments, analyzing the biological barrier to determine the amount of the analyte of interest retained in the biological barrier comprises mass spectrometry analysis of the biological barrier. In particular embodiments, the biological barrier comprises a dermal or epidermal membrane. In specific embodiments, the biological barrier comprises oral cells, gastrointestinal cells, buccal cells, ocular cells, nasal cells, respiratory cells, vaginal cells, tumor cells, mucus cells or biofilm cells.

In certain embodiments the second plurality of wells contain a receptor fluid and the method further comprises: allowing the compound to permeate through the biological barrier and into the second plurality of wells, wherein the compound and the receptor fluid in the second plurality of wells is a permeated liquid; and analyzing the permeated liquid to determine an amount of the analyte of interest. Particular embodiments further comprise removing the permeated liquid from the second plurality of wells prior to analyzing the permeated liquid to determine the amount of the analyte of interest.

In specific embodiments, analyzing the permeated liquid to determine the amount of the analyte of interest comprises high-performance liquid chromatography (HPLC), liquid chromatography—mass spectrometry (LC-MS), mass spectroscopy, spectrophotometry, ultraviolet—visible spectroscopy or fluorescence spectroscopy and microscopy or radioactivity. In particular embodiments, the period of time is at least one hour, and in some embodiments the period of time is at least eight hours. In certain embodiments, the liquid comprises Sulforhodamine B.

In specific embodiments, the first plurality of wells and the second plurality of wells each comprise at least 96 wells. In particular embodiments: the first plurality of wells is configured in a first planar array; the second plurality of wells is configured in a second planar array; and the method further comprising clamping the first planar array to the second planar array.

Exemplary embodiments also include an apparatus comprising: a first plurality of wells configured in a first planar array; a second plurality of wells configured in a second planar array; a biological barrier between the first plurality of wells and the second plurality of wells; a compound contained in the first plurality of wells, wherein the compound is in contact with the biological barrier and meant to be tested; and a device configured to analyze the biological barrier to determine an amount of the analyte of interest retained in the biological barrier. Certain embodiments may also include a receptor fluid contained in the second plurality of wells, wherein the receptor fluid is in contact with the biological membrane and meant to be analyzed.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "approximately, "about" or "substantially" mean, in general, the stated value plus or minus 10%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 14 illustrates a two-step process for determining whether to include full epidermis samples based on permeation and whether the dermis is a systemic delivery candidate of a local delivery candidate.

FIG. 15 illustrates types of formulation libraries that can be obtained and included in the permeation and retention screening.

DETAILED DESCRIPTION OF EXEMPLARY EMBODIMENTS

Embodiments of the high-throughput formulation screening method (HTS) disclosed herein include methods used to directly measure the permeation or amount of drugs, formulations or compounds across and into membranes, importantly the skin with the use of spectroscopic and microscopic techniques.

Figure 1:
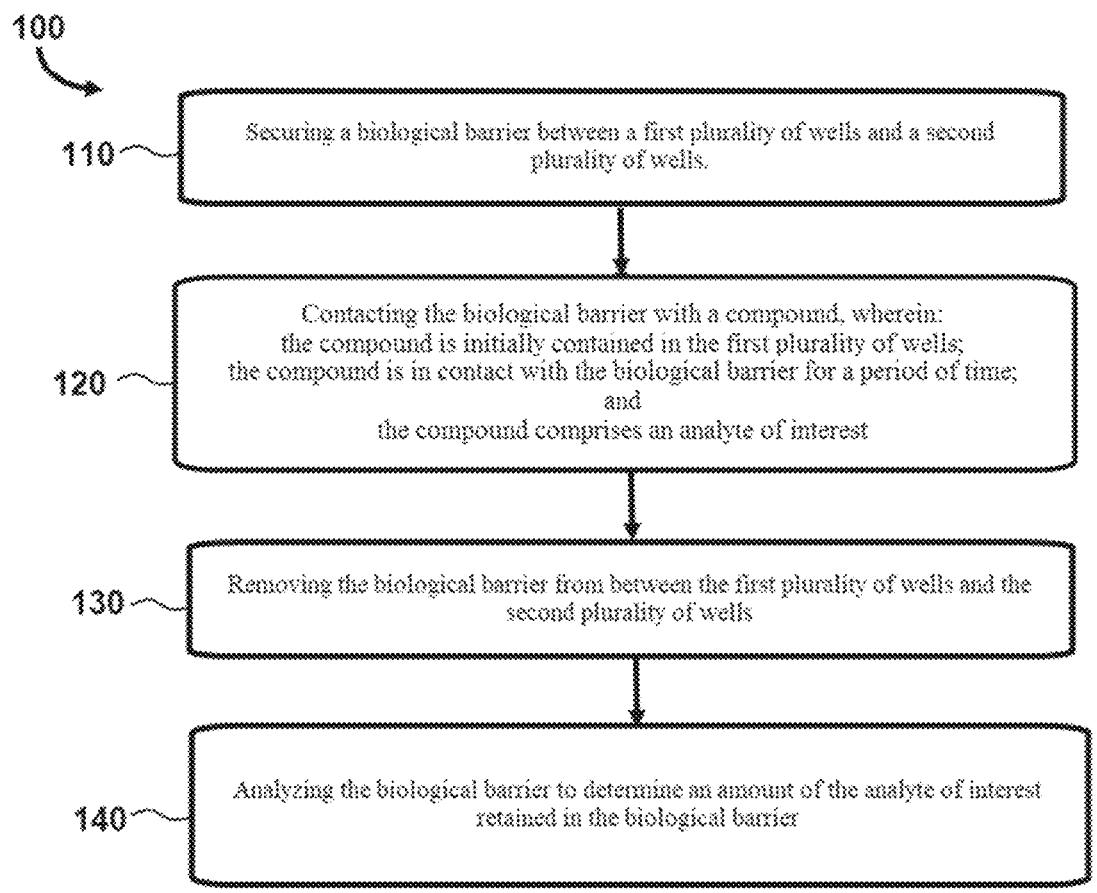
FIG. 1 illustrates an overview of a method 100 according to an exemplary embodiment is provided in flowchart format.

Referring initially to FIG. 1, an overview of a method 100 according to an exemplary embodiment is provided in flowchart format. As shown in FIG. 1, method 100 comprises a step 110 of Securing a biological barrier between a first plurality of wells and a second plurality of wells. In addition, method 100 comprises a step 120 of contacting the biological barrier with a compound. In particular embodiments, the compound is initially contained in the first plurality of wells; the compound is in contact with the biological barrier for a period of time; and the compound comprises an analyte of interest. Particular embodiments may include a receptor fluid in the second plurality of wells. In the embodiment shown, method 100 further comprises step 130 of removing the biological barrier from between the first plurality of wells and the second plurality of wells. Method 100 also comprises step 130 of analyzing the biological barrier to determine an amount of the analyte of interest retained in the biological barrier. It is understood that the steps disclosed in FIG. 1 are merely exemplary of one embodiment and that additional embodiments of the present disclosure may comprise additional or fewer steps than provided in FIG. 1

As used herein, a biological barrier is defined as a membrane that limits the diffusion of a molecular entity such as a drug. Examples of membranes of particular interest are cellular or non-cellular barriers, such as human skin, nasal, olfactory, respiratory, lung, oral, buccal, vaginal, ocular mucosas or other epithelial and non-epithelial barriers, including endothelial barriers. A membrane can include biological and natural membranes or synthetic membranes, from human origin or non-human origin. It can also include parts of epithelial and non-epithelial barriers. In the case of the skin, it can include the epidermal layer only or the dermal layer only. Additional biological barriers include those like mucus, microbiological biofilms, extracellular fluid, hydrogel networks and the like.

Embodiments of the HTS method can improve the efficiency of in vitro permeation testing (IVPT) and speed drug development by being able to directly analyze at least 96 different samples in one day. This method is needed for the development and optimization of formulations and drug delivery technologies, including devices, for the analysis of drug products, cosmetics, personal care products, consumer products, and pesticides. It can as well be used for fine-tuning molecules for tissue permeation and retention in a specific layer of the skin, for comparison of novel formulations with marketed products, selection of dosage form, dose and type of penetration enhancer, reverse engineering of formulations, as well for aid in post-marketing claims and selection of formulation for MUsT trials.

The HTS system can be comprised of two 96-well plates with and/or without bottom with a membrane in between to measure the permeability and amount of compounds across and into the skin. The plates used can be 96-well microplates made of polystyrene with no bottom. These plates can be similar to those provided by microwell plate manufacturers such as Greiner bio-one and have a microwell diameter of 6.96 mm. The volume of each microwell can be, for example, 380 µL and the area of diffusion can be approximately 0.38 cm². The wells can be fabricated to have different diffusion areas, volume or different composition or can be acquired by a different manufacturer.

The dimensions of the plates can be modified and a higher number of microwells can be added to increase the throughput of the method.

The microwells need to be leveled up in order to ensure sufficient sealing and no lateral diffusion between samples. Exemplary embodiments include a raised ridge or flange around the perimeter of the well which is in contact with the membrane. This ridge or raised flange should be greater than 500 microns but less than 2000 microns, for example. Example 6 shows an example of utilizing squared 384-well plates with no raised ridges separating the microwells or ridges on the perimeter of the wells.

The bottom plate (receptor/receiving compartment) is filled with a preferably degassed medium that mimics physiological conditions and allows the determination of permeation of drug or compounds across the skin, into the systemic circulation. The medium can also be called receptor fluid and it usually mimics physiological conditions. A commonly used medium is PBS (pH=7.4), however, this can be changed by the addition of surfactants or any other solvent to maintain sink conditions. The membrane/tissue (e.g. skin) is placed on top of the receptor compartment and the upper bottomless plate (donor compartment) is placed on top of the skin. The plates have at least 2 symmetric, corresponding and parallel holes in each side of the plate to ensure proper sealing between the plates and the membrane located between them. Preferably 3 holes, more preferably 4 holes, most preferred 6 holes. This allows the plates to be assembled together in the format of a sandwich design. Preferably a minimum of approximately 4 kg weight should be placed on top to avoid leakage or lateral diffusion, when an 8×9 cm skin tissue is used as a sample. A maximum weight for this size device is 40 kg. The weight to be applied is a function of the size of the membrane used. When human skin is used, the applied weight will be no less than 0.05 kg/cm² and no more than 0.5 kg/cm². The pressure applied on top avoids leakage between the wells and cross-contamination of the samples.

The applied pressure can be achieved using several ways. Spring loaded clamps that apply the force between the two plates. The force can also be applied using weights provided with the device that are placed on the upper plate during assembly until the plates have been connected using a screw mechanism through the above mentioned symmetric, corresponding and parallel holes in each side of the plate.

The method can be used with 2 bottomless plates instead of 1 bottomless plate and 1 plate with bottom when large skin samples are used. This further avoids cross-contamination between samples by allowing the removal of the receptor fluid before disassembling the plates. In the case 2 bottomless plates are used, a sealable adhesive film can be used to cover the receptor compartment/plate.

The receptor fluid can be analyzed by high performance liquid chromatography (HPLC), spectroscopy, LC/MS, or any other analytical technique. The skin tissue can be analyzed by microscopy, spectrophotometry including but not limited to two-photon or multiphoton microscopy, Raman spectroscopy or microscopy, Confocal-Raman microscopy, Mass spectrometry, MALDI (Matrix Assisted Laser Desorption/Ionization), RAMAN-IR, or tomographies.

Figure 2:
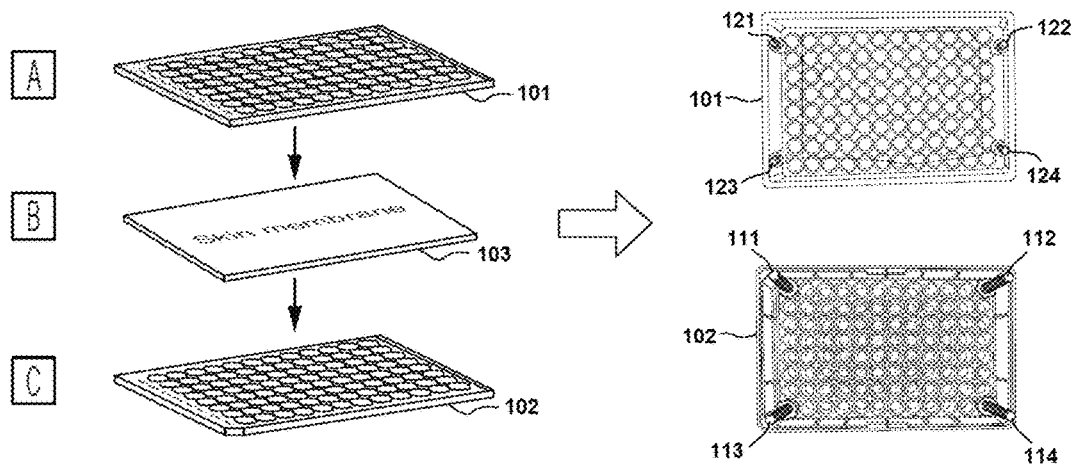
FIG. 2 illustrates a schematic representation of an apparatus for use in performing the methods disclosed herein, including the embodiment of FIG. 1.

Referring now to FIG. 2 a schematic representation of an apparatus is shown for use in performing the methods disclosed herein. The embodiment shown comprises a 96-well plate assembly with a bottomless plate 101 (donor compartment) on top (A) and 96-well plate 102 with bottom (receptor compartment) at the bottom (C). The biological barrier (e.g. skin 103 membrane) is placed in between the plates 101 and 102 (B). In this embodiment, the stratum corneum (SC) facing the donor plate 101 and the dermis facing the receptor plate 102.

Figure 3:
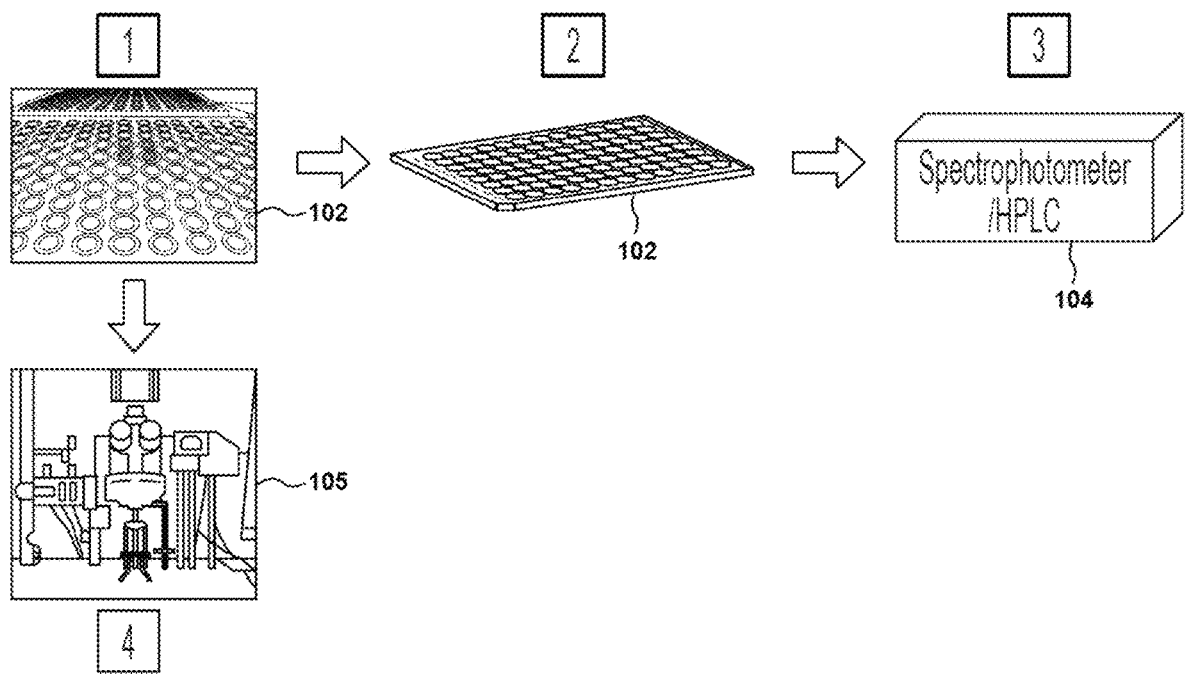
FIG. 3 illustrates a schematic representation of an apparatus for use in performing the methods disclosed herein, including the embodiment of FIG. 1.

Referring now to FIG. 3, the bottom plate 102/receptor compartment (C) can be further analyzed. As explained in more detail below, in certain embodiments the bottom plate/receptor compartment (element 102 in FIG. 3) can be analyzed for permeation of Sulforhodamine B (SRB) across the skin using a spectrophotometer (element 104 in FIG. 3). In addition, the skin tissue (element 103 in FIG. 3) can be analyzed for SRB retention using a multiphoton microscope (element 105 in FIG. 3).

Sampling:

For screening purposes, sampling can be done at the end of the experiment, which can take up to 72 hours, preferably 6-24 hours.

Samples are first taken from the receptor compartment by punching the adhesive film. Removing the sample prior to disassembling the plates avoids cross contamination between the microwells/samples.

Sampling can also be done at predetermined timepoints as long as 2 bottomless plates are used and the receptor compartment is covered with an adhesive film and receptor fluid added after every sampling time-point.

Skin Retention Quantification

Quantification of the amount of compounds permeated into the skin can be accomplished by optical techniques such as microscopy or spectroscopy, including tomographies or by solvent extraction techniques.

After removal of the receptor fluid, the remaining compositions on the donor plate can be removed. The donor wells are washed with PBS (pH=7.4) or other adequate medium and tapped dry with a Kimwipe™ per well.

The plates are disassembled and the skin can be placed on the two-photon microscope stage. The stage is automated and connected to a computer. The distance between each well can be added to the software to move from sample to sample and speed the analysis. Quantification of the compounds in the skin can be made from 0 to at least 300 micrometers deep into the skin. The optical sectioning can be done at every 1 micrometer deep into the skin.

For 2-photon microscopy, the amount of compounds can be analyzed at every 1 micrometer into the skin. The pathway by which drugs or compounds enter the skin can also be visualized by having different channels that detect different emission wavelengths. This makes it easier to separate the skin autofluorescence from the compound fluorescence.

Microscopic and spectroscopic methods not based on fluorescence can also be used to determine the amount of drug in the skin.

Confocal-Raman microscopy can be used the same way with the difference that it does not penetrate deep into the skin. Making possible only measurements of 20 to 100 micrometers, to a few hundred micrometers.

Microscopic and spectroscopic methods not based on fluorescence can also be used to determine the amount of drug in the skin. For Raman microscopy and spectroscopy, including the Raman pen, the measurement can be done to at least 20 micrometers. The devices disclosed in PCT Patent Application Publications WO 2018/045208 and WO 2018/227079 can also be used to measure the amount on the top layers of the skin.

For methods that do not have high tissue penetration potential, the skin can be measured on top and then flipped upside down and measure on the bottom. Correlations between the amounts of compounds on top versus the bottom can be made to determine changes in skin retention and permeation.

In certain exemplary embodiments, other optical techniques such as RAMAN-IR, FT-IR, MALDI, MALDI-MSI can also be used. In particular embodiments, the system is automated to increase the throughput of the method.

In exemplary embodiments, the microwell plates can be obtained from any manufacturer or can designed de novo before use. The plates should avoid lateral diffusion and each plate should have projected microwells to ensure proper sealing (See example 6). Flattened and not projected microwells may result in lateral diffusion and cross-contamination of the samples.

The plates should be facing each other, not piled on each other. The dimensions can change but also include 6, 24, 96, 384, and 1586-well plates. Preferably the microwells are slightly separated from each other. The plates should be incubated at no more than 32 deg C. to avoid the formation of blisters (See Example 1). The pressure applied on top of the plates ensures sealing of the plates (see working examples discussed herein).

Exemplary methods can also be automated by the use of robotic or computerized systems that manually assemble the plates, or remove samples and aid in the analysis of either the receptor fluid or the skin tissue.

The High-throughput screening methods disclosed herein help to develop and optimize formulations, including generic drug products by comparing its generic equivalent which could help in bioavailability/bioequivalence studies, for drug delivery purposes across biological barriers. Exemplary embodiments can help to select a dosage form, the vehicle (excipients grades, manufacturer and concentrations, polymers, permeation enhancers, solvents), or dose.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

These were the first experiments performed to assess the feasibility of using commercialized 96-well plates. The donor/upper plate 101 was bottomless from Greiner bio-one with an area of diffusion of 0.38 cm$^2$ and 380 μL volume. Sulforhodamine B (SRB) was used as a model hydrophilic fluorescent probe, and Rhodamine B hexyl ester (RBHE) was used as model lipophilic fluorescent probe.

Two symmetric and parallel holes 121 and 122, and 123 and 124 were designed in each side of the microwell-plates using a drill. The receptor plate 102 (with bottom) was overfilled with PBS:Ethanol (80:20, v/v) and the skin 103 was placed on top, dermis side down in contact with the receptor compartment and stratum corneum up. The donor/upper 101 plate 101 were placed upside down, on top of the skin 103. This sandwich was assembled with four screws 111-114 (2 on each side of the well), manually. The assembly was placed on a shaker incubator at 37 deg C. and 75 rpm to equilibrate for 1 hour.

After 1 hour, 50 μL of 0.5 mg/ml and 0.05 mg/ml SRB in PBS:Ethanol (80:20) as well as 50 μL of 0.05 mg/ml of RBHE in PBS:Ethanol (80:20) were applied in the donor compartment, on top of the skin. The plate was covered with parafilm and aluminum foil and placed on the shaker incubator at 37° C., 75 rpm for 24 hours. After 24 hours, SRB and RBHE solution were removed from the donor plate and each microwell was washed with 100 μl of PBS, 3 times and tapped dry with Kimwipes™ to avoid any contamination. The plates were disassembled and although there seem to not have been any lateral diffusion, some blisters were formed which could have been due to higher temperature on top of the skin (37° C.).

Figure 4:
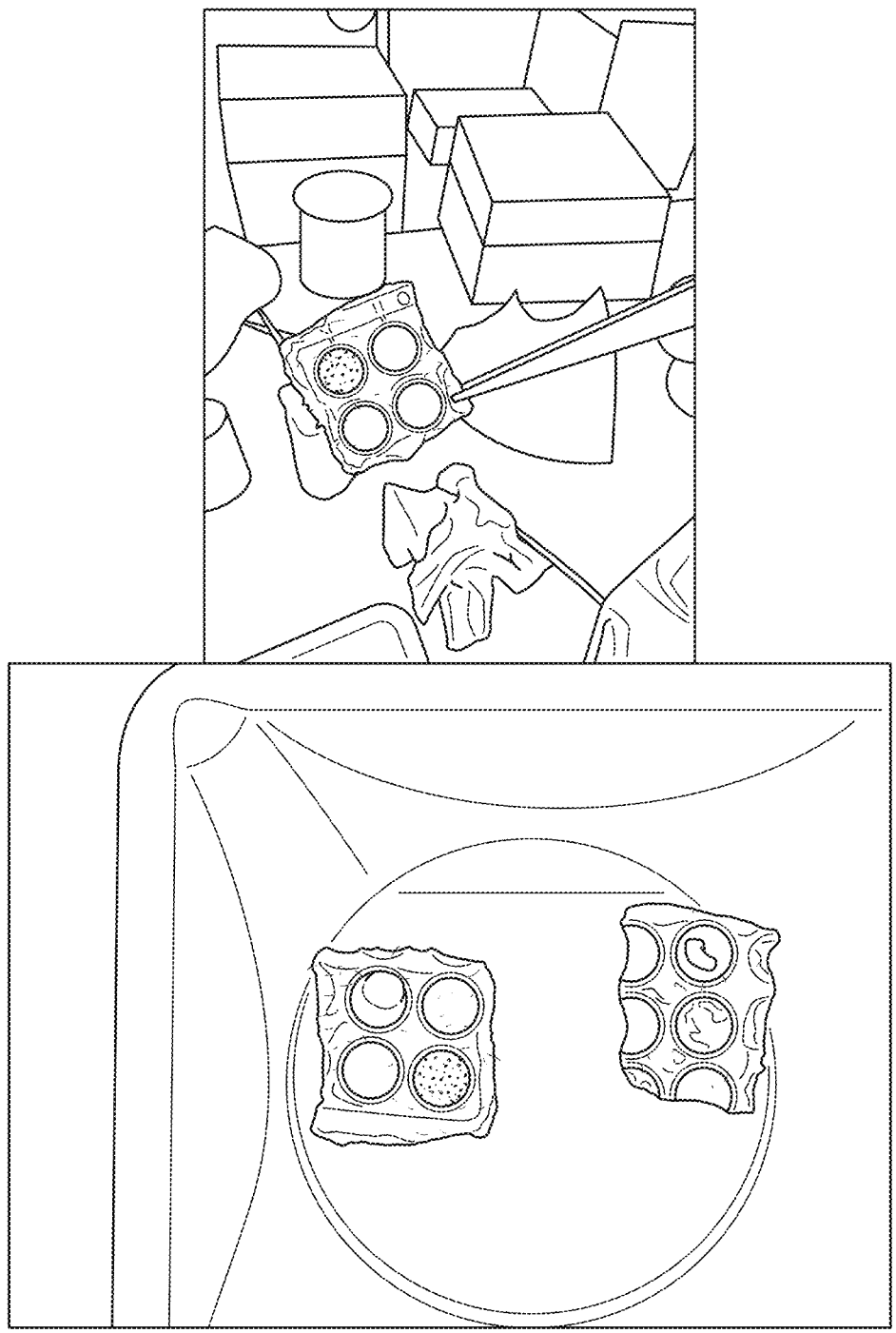
FIG. 4 illustrates a photograph of a biological barrier analyzed according to an exemplary embodiment of a method as disclosed herein.

As shown in FIG. 4, there was no lateral diffusion but at 37° C. formed some blisters. The plates were manually screwed and no weight added resulting in an unknown force or weight applied to the biological barrier placed between the plates.

Example 2

These were the first experiments performed to assess the feasibility of using commercialized 96-well plates. The donor/upper plate was bottomless from Greiner bio-one with an area of diffusion of 0.38 cm$^2$ and 380 μL volume. Sulforhodamine B (SRB) was used as a model hydrophilic fluorescent probe, and Rhodamine B hexyl ester (RBHE) was used as model lipophilic fluorescent probe.

Figure 5:
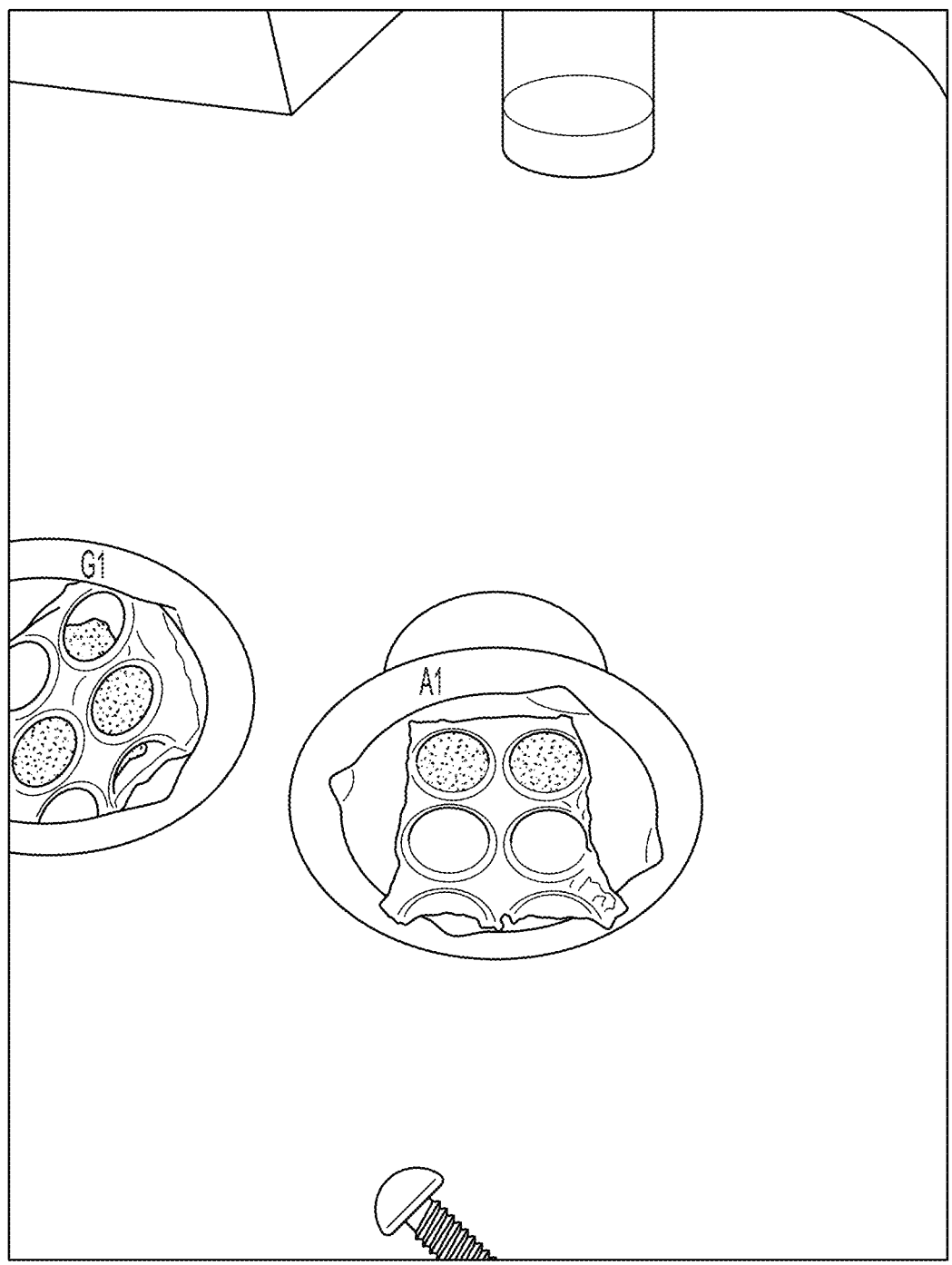
FIG. 5 illustrates a photograph of a biological barrier analyzed according to an exemplary embodiment of a method as disclosed herein.
Figure 6:
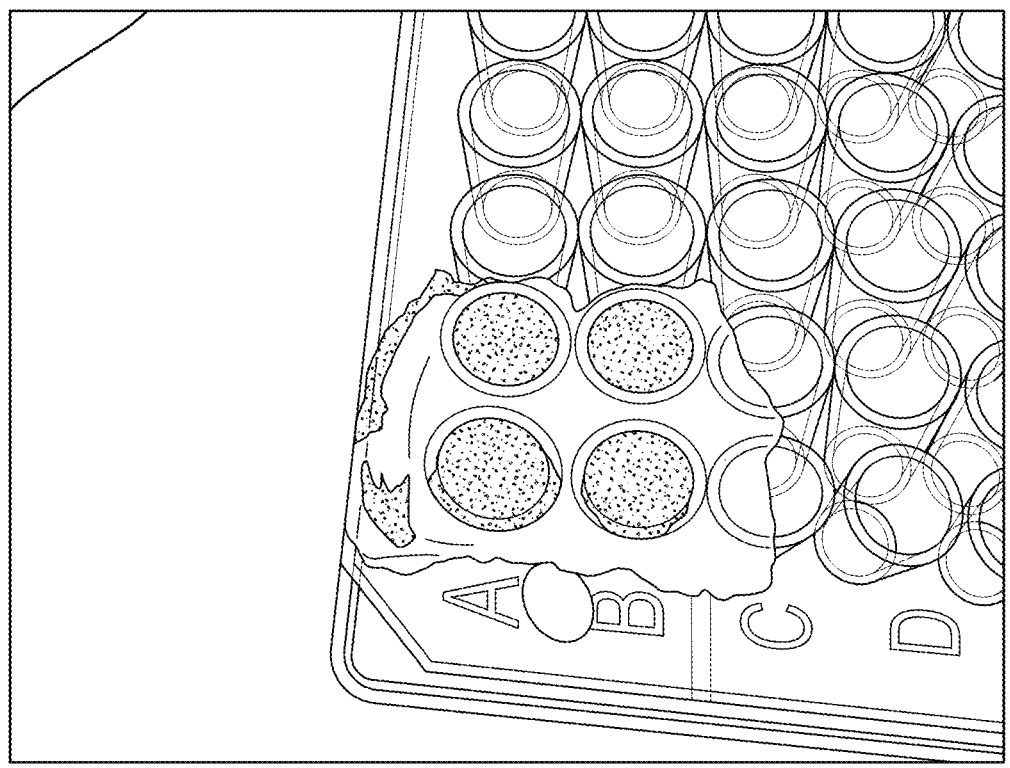
FIG. 6 illustrates a photograph of a biological barrier analyzed according to an exemplary embodiment of a method as disclosed herein.

Two symmetric and parallel holes were designed in each side of the microwell-plates using a drill. The receptor plate (with bottom) was overfilled with PBS:Ethanol (80:20, w/v) and the skin was placed on top, dermis side down in contact with the receptor compartment and stratum corneum up. The donor and bottomless plate were placed upside down, on top of the skin. A weight of approximately 500 g was placed on top of the sandwich. Screws were added. 50 μl of SRB was applied at 2 different concentration (0.5 mg/ml and 0.05 mg/ml in PBS:Ethanol (80:20, w/v)-A1- and 50 μl of RBHE was applied at 0.2 mg/ml and 0.02 mg/ml in PBS:Ethanol (80:20, w/v)-G1-on the donor plate, on top of the skin. The donor wells were covered with parafilm and the plates were covered with aluminum foil. The HTS was placed on a shaker incubator at 37 deg C. and 75 rpm. After 24 hours, each sample was washed with 100 μl of PBS, 3 times and tapped dry with Kimwipes™ to avoid any contamination. The plates were disassembled and, as shown in FIG. 5, it was noticed that there was leakage between the wells due to the plates not being completely sealed.

Example 3

The same type of plates as those used in Examples 1 and 2 were used to assemble the HTS method with the skin tissue in between the plates for Example 3.

The receptor wells were overfilled with PBS:Ethanol (80:20). Each skin sample was placed on top of those wells and the donor compartment (bottomless plate) was placed on top of the skin. A weight of 714 g was placed on top of the sandwich and 4 screws were tight to the same level of compression as the weight. The assembly was put on a shaker incubator at 32° C. to avoid blisters and 75 rpm for 1 hour to equilibrate the temperature.

After 1 hour, 50 μl of SRB 0.5 mg/ml in PBS:Ethanol (80:20) was added to the donor wells and the HTS was placed on a shaker incubator at 32 deg C. and 75 rpm. After 18 hours, excess of SRB was removed from the wells and each well was washed with 200 μl of PBS (pH=7.4) and each well was blotted dry with a Kimwipes™. Leakage occurred between the wells and samples.

Example 4

The example conducted a comparison between methods. The same plates as those used in the Examples 1-3 were used to develop the HTS method.

"The 96-well plates, with and without bottom, were modified by inserting 2 symmetric and parallel holes in each side of the plate using a drill. The holes were made in order to attach the plates together as a sandwich. The skin was tape-stripped 15 times, rubbing with a thumb three times before each strip (in the same manner as for the Franz cells). Tape-stripping was necessary to allow for drug permeation across the skin and direct quantification in the receptor compartment. SRB is unable to permeate intact skin and previous studies have shown that the total or partial removal of the stratum corneum would enhance permeation across the whole skin (Andrews et al., 2013). The receptor fluid analysis was needed to compare permeability of SRB between methods (FC and HTS)."

"The 96-well plate with the bottom was used as the receptor compartment. The volume of each well is 380 μL and the area of diffusion is 0.38 cm$^2$. The receptor compartment was overfilled with degassed PBS (pH=7.4) to avoid the formation of any bubbles that would hinder drug permeation. The skin was placed on top, stratum corneum up and dermis down, in contact with the receptor fluid. It was observed that if we overfilled the plate with the medium and placed the skin on top of it, bubbles formation would be avoided. The bottomless 96-well plate was used as the donor compartment. The donor plate was placed on top of the skin, as seen in FIG. 3. Using a force gauge, a known force of 1.15 kg was applied to maintain the plates sealed without damaging the skin based on prior optimization. Screws were added to maintain the plates sealed. The weight applied was previously tested at different forces to assure that it would not damage the skin and form blisters by applying high forces or that it would not leak and/or laterally diffuse by applying low forces. The weight selected maintains the plates sealed together, without the formation of bubbles or blisters or without the presence of leaking or lateral diffusion of the drug/formulation to be tested. Preliminary studies showed that drug permeation did not occur to the adjacent wells through lateral diffusion during the time course of these studies (Fig. S1) either by visualization, receptor fluid analysis of adjacent wells containing only PBS or through 2-photon microscopy where nothing can be observed through the microscope and only baseline to no fluorescence intensity was being detected.

The plate was incubated at 32° C. for 1 h. After equilibrating the temperature, 50 μL of SRB (0.5 mg/ml) was applied in quadruplicate on top of the skin and 50 μL of PBS (pH=7.4) in duplicate was applied as a control. The skin was incubated for 8 h, at 32° C. and 75 rpm in a shaker incubator. After 8 h, the plates were disassembled and the receptor plate was analyzed using a spectrophotometer (Infinite M200 microplate reader, TECAN US Inc, NC, USA) for the quantification of fluorescence intensity (λexcitation=550 nm and λemission=590 nm). Standard solutions of SRB in PBS (pH=7.4) in the range of 500-0.03 μg/ml were prepared and the fluorescence intensity was measured to obtain the calibration curve. The linearity range was between 3.95 and 0.1

μg/ml (R2=0.9982).".-from Martins P P, Estrada A D, Smyth H D. A human skin high-throughput formulation screening method using a model hydrophilic drug. International journal of pharmaceutics. 2019 Jun. 30; 565:557-68.

Figure 7:
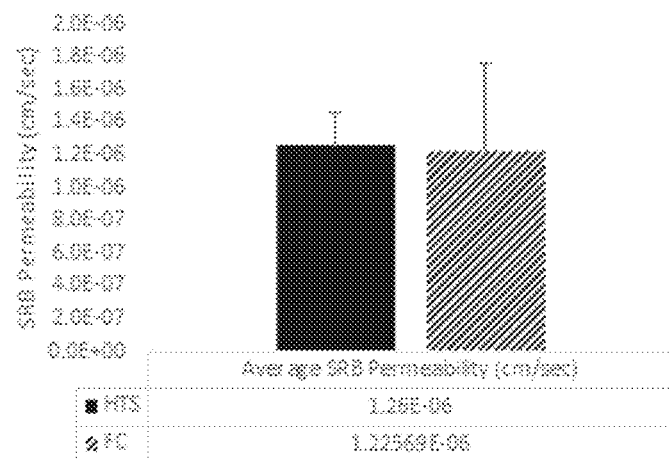
FIG. 7 illustrates a graph showing similarity between Franz Cells (FC) and high throughput screening (HTS) in permeability of Sulforhodamine B (SRB) across the skin.

Surprisingly, it was found that despite the different devices, the permeation and distribution of the drug was almost identical between Franz cells and HTS. Similarity between Franz Cells (FC) and HTS in permeability of SRB across the skin (p-value >0.05) is shown in FIG. 7.

Skin Retention Analysis:

A two-photon-induced fluorescence imaging was used to determine the retention of SRB in the skin using a Prairie Technologies UltimaIntravital 2PA confocal microscope system (Park et al., 2008; Denk et al., 1990). The microscope objective was an Olympus® 10×, 0.30 NA, UMPlanFL N water immersion lens. Two-photon laser excitation was provided by a Spectra-Physics Tsunami® Ti:Sapphire laser with a $\tau P=150$ fs and $P=108$ mW. The laser was tuned to 1000 nm, since SRB excites at 550 nm and no skin autofluorescence is observed at this wavelength. Four fluorescence channels were detected simultaneously during imaging. The photomultiplier tube (PMT) bias voltages for each channel were set to 650 V for channel 1, 650 V for channel 2 (where SRB is detected), 800 V for channel 3 (where we can measure the autofluorescence of the skin), and 800 V for channel 4. Skin autofluorescence or second harmonic generation of collagen were detected in channels 3 and 4, respectively (Roberts et al., 2011). The fluorescence emission of SRB was recorded in channel 2 ($\lambda=595\pm35$ nm) since the wavelength of emission for SRB is 590 nm. Skin images were recorded above the surface of the skin and the maximum fluorescence intensity was considered to be the top layer or surface of the skin since excess of formulation was still present at the top of the skin at the end of the permeation study (8 h). The z-axis profile was recorded using 5 μm steps from the surface of the skin down to 150 μm.

For both methods, images were recorded at 512×512 pixels. For this reason and because what we want to measure is the relative change in intensity as a function of depth, and not the absolute value, the relative fluorescence intensity values were calculated based on the obtained absolute fluorescence intensity from each sample and at each depth—from Martins P P, Estrada A D, Smyth H D. A human skin high-throughput formulation screening method using a model hydrophilic drug. International journal of pharmaceutics. 2019 Jun. 30; 565:557-68.

Figure 8:
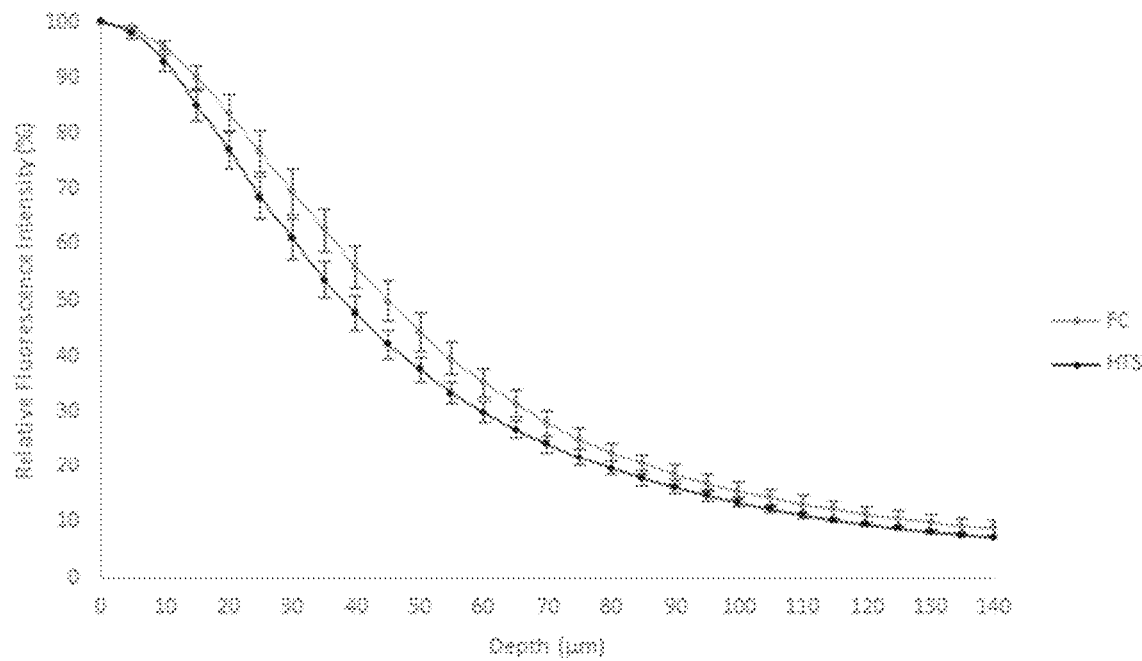
FIG. 8 illustrates a graph showing the depth profile/Z-axis profile regarding a similar relative change in fluorescence intensity of Sulforhodamine B (SRB) over every 5 μm depth in the skin when permeation studies were conducted using FC and HTS.

The depth profile/Z-axis profile regarding the relative change in fluorescence intensity of SRB over every 5 μm depth in the skin when permeation studies were conducted using FC and HTS was similar as shown in FIG. 8.

Example 5

This example evaluated the high-throughput capacity of the method and effect of solvent and surfactants on each layer of the skin.

Figure 9:
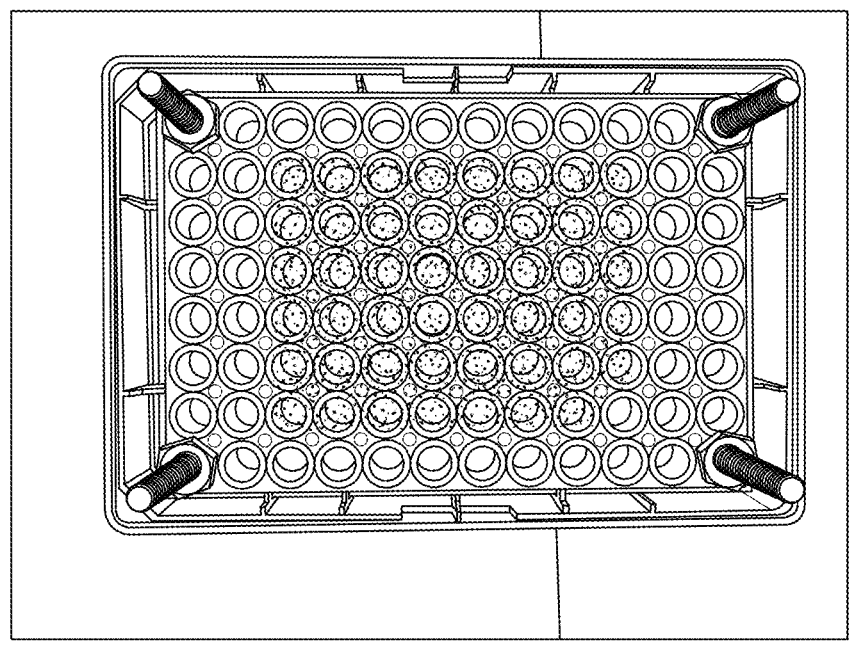
FIG. 9 illustrates an assembly of an apparatus according to an exemplary embodiment of the present disclosure.

Two bottomless 96-well plates from Greiner bio-one were used. The corner wells were used to insert the screws for plate assembly as shown in FIG. 9.

The receptor plate was sealed with an adhesive film and overfilled with PBS (pH=7.4).

An 8×9 cm of skin tissue was placed on top of the receptor plate, dermis side in contact with the receptor fluid and stratum corneum up. The donor plate was placed on top of the skin. A 4 kg weight was placed on top and nuts were attached to the plate.

This sandwich was incubated for 1 hour at 32 deg C. and 75 rpm. After 1 hour, the formulations prepared in Table 1 and containing 0.5 mg/ml of SRB as a model hydrophilic drug were applied in triplicate to the donor wells.

The receptor compartment was analyzed by fluorescence using a plate reader and the skin was analyzed using 2 photon microscopy, the same way as described in Example 4. Images were collected at 256×256 pixels and 223.78 μm×223.78 μm. The z-axis profile was obtained by acquiring images at every 10 μm down the skin, up to 200 μm. The detailed 2-photon analysis utilized in this study took approximately 2 h (around a minute to 2 min for each well).

A 3×2×3 full factorial design was used to design the experiment and statistically analyze the differences in permeation and retention of the formulations applied in the skin.

The data was able to provide valuable information on what type of factors influence retention in each skin layer. This seems to be the first time that a high-throughput screening was published that shows the factors that are important at each skin layer. By factors we mean, surfactant concentration, type and solvent ratio. Table 2 shows that both surfactant concentration and solvent ratio have a significant impact on the retention profile of SRB inside the skin.

A post hoc analysis also showed that 5% and 2.5% surfactant concentration increases the amount of SRB inside the skin when compared to no surfactant in the formulation. For solvent ratio, using dimethyl sulfoxide (DMSO) alone enhances the amount of the model drug in all the skin layers when compared to a 50:50 mixture of DMSO:Propylene glycol.

In addition, and only at lower depths (100-150 micrometers) DMSO significantly enhance the amount of SRB into the skin when compared to Propylene glycol alone.

TABLE 1

Composition of solutions to be screened using the HTS method

| Formulation number | Solvent ratio (PG:DMSO) | Surfactant type (HLB) | Surfactant concentration (% (w/w)) |
|---|---|---|---|
| 1 | 100:0 | Oleic Acid | 0 |
| 2 | 100:0 | Oleic Acid | 2.5 |
| 3 | 100:0 | Oleic Acid | 5 |
| 4 | 100:0 | Tween 80 | 0 |
| 5 | 100:0 | Tween 80 | 2.5 |
| 6 | 100:0 | Tween 80 | 5 |
| 7 | 50:50 | Oleic Acid | 0 |
| 8 | 50:50 | Oleic Acid | 2.5 |
| 9 | 50:50 | Oleic Acid | 5 |
| 10 | 50:50 | Tween 80 | 0 |
| 11 | 50:50 | Tween 80 | 2.5 |
| 12 | 50:50 | Tween 80 | 5 |
| 13 | 0:100 | Oleic Acid | 0 |
| 14 | 0:100 | Oleic Acid | 2.5 |
| 15 | 0:100 | Oleic Acid | 5 |
| 16 | 0:100 | Tween 80 | 0 |
| 17 | 0:100 | Tween 80 | 2.5 |
| 18 | 0:100 | Tween 80 | 5 |

TABLE 2

Statistically significant variables on the amount of SRB retained at each layer of the skin (*) = p-value < 0.05 and (**) = p-value < 0.01).

| Skin depth (μm) | Factor | Skin layer |
|---|---|---|
| 0 | Solvent ratio (*) | SC 0-20 μm |
|  | Surfactant concentration (**) | Viable Epidermis |
| 20 | Solvent ratio (**) | <50-100 μm |
|  | Surfactant concentration (*) | Dermis up to |
| 50 | — | 4 mm |
| 100 | Solvent ratio (*) |  |
|  | Surfactant concentration (*) |  |
| 150 | Solvent ratio (**) |  |

Figure 10:
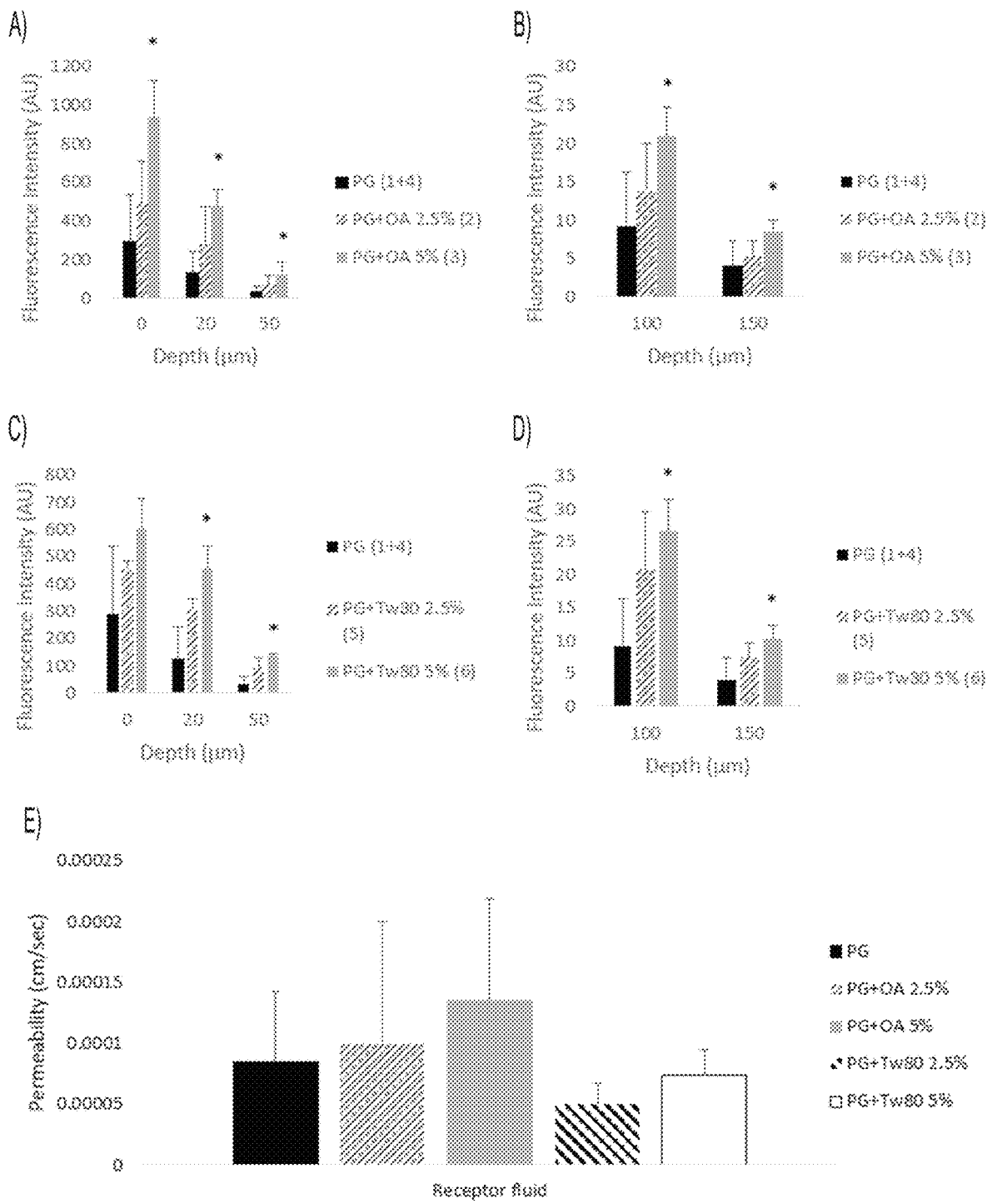
FIG. 10 illustrates graphs showing the effect of surfactant concentration and surfactant type on Sulforhodamine B (SRB) permeation and retention across and into the skin.

FIG. 10 illustrates the effect of surfactant concentration and surfactant type on SRB permeation and retention across and into the skin. FIG. 10 panels (A) and (B) correspond to the absolute fluorescence intensity of SRB in the skin at different depths after the use of PG alone or in combination with 2.5% and 5% oleic acid (OA). FIG. 10 panels (C) and (D) correspond to the absolute fluorescence intensity of SRB in the skin at different depths after the use of PG alone or in combination with Tween 80 2.5% and 5%. FIG. 10 panel (E) corresponds to the permeability of SRB across the skin, into the receptor fluid of PG alone or in combination with surfactants (*=p<0.05).

For both surfactants, the higher its concentration the higher amount of drug that can be quantified inside the skin. In addition, if we compare to the permeability across the skin, panel (E), although not statistically significant, shows that the amount permeating into the receptor fluid may have a different behavior depending on the surfactant used. Indeed, using OA in the formulation increased the amount of drug inside the skin and also across the skin, into the receptor solution. Increasing the concentration of Tween 80 increased the amount of SRB inside the skin but not across the skin indicating a possible retardation effect. This hypothesis would need to be explored in further studies since no statistically significant data was obtained, not for the receptor fluid analysis and neither for surfactant type—From Martins P P, Estrada A D, Smyth H D. A human skin high-throughput formulation screening method using a model hydrophilic drug. International journal of pharmaceutics. 2019 Jun. 30; 565:557-68.

Example 6

Figure 11:
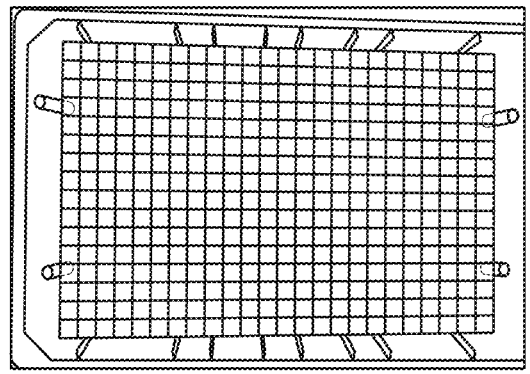
FIG. 11 illustrates an apparatus for a 384-well plate-based high-throughput screening method and the position of the high concentration and low concentration SRB in the 384-well plate.

Feasibility studies were conducted using squared and flat 384-well plates with no ridges or projected wells. The plates were assembled the same way as presented in Example 4. Each microwell had an area of diffusion of 0.144 cm$^2$. SRB was also used as a model hydrophilic drug at two different concentrations: 0.5 mg/ml and 0.125 mg/ml in PBS (pH=7.4). FIG. 11 shows the 384-well plate-based high-throughput screening method and the exact position of the high concentration and low concentration SRB in the 384-well plate. Samples were taken after 8 h and measured using fluorescence in a plate reader.

Figure 12:
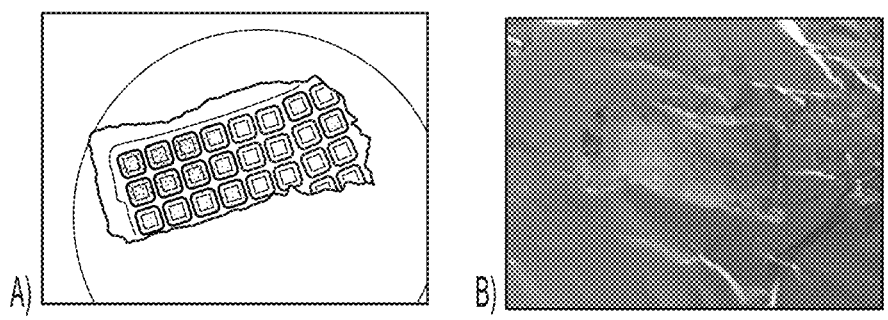
FIG. 12 illustrates a skin sample used in a method utilizing the apparatus of FIG. 11.

FIG. 12 illustrates a skin sample used in the feasibility in vitro permeation study using 384-well plates. Lateral diffusion is evident in between the squared and flattened wells. FIG. 12 panel (A) shows the skin sample with epidermis up and FIG. 12 panel (B) shows the skin sample with dermis up.

Even though lateral diffusion was present, the permeability of SRB across the skin changed between the 0.5 mg/ml SRB and the 0.05 mg/ml SRB applied on the skin and seems reasonable.

Figure 13:
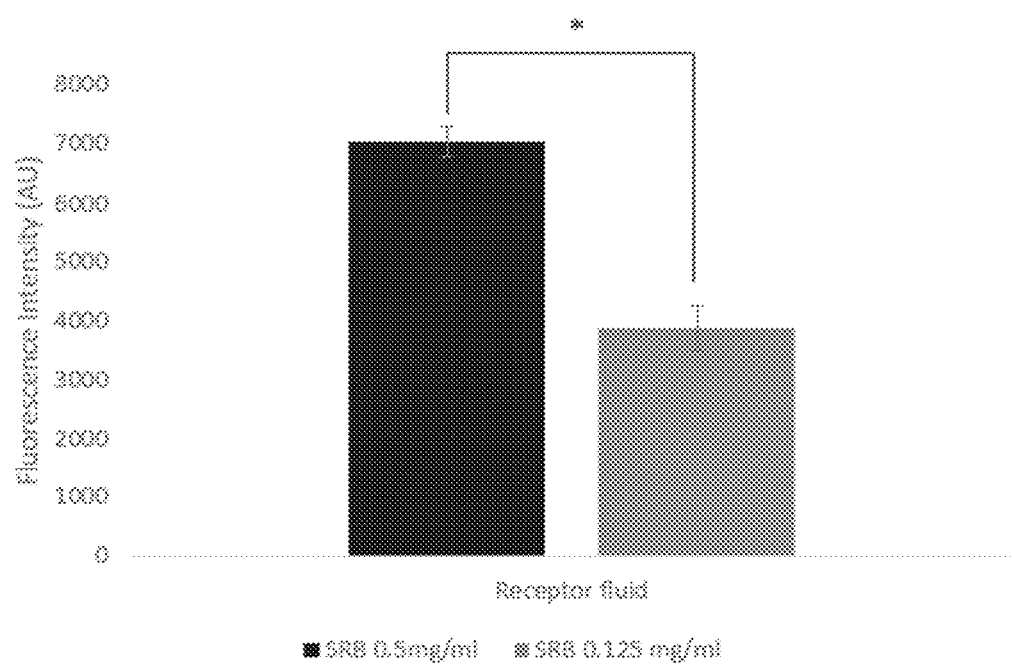
FIG. 13 illustrates a graph showing the fluorescence intensity (AU) of SRB 0.5 mg/ml and SRB 0.125 mg/ml across the sample of FIG. 12.

FIG. 13 illustrates a graph showing the fluorescence intensity (AU) of SRB 0.5 mg/ml and SRB 0.125 mg/ml across the skin using 384-well plates (*=p<0.05).

Example 7

As shown in FIG. 14, this example illustrates a two-step process for determining whether a drug and/or formulation will be preferred as a systemic delivery candidate or a local delivery candidate. The two steps involve testing permeation through the human epidermal membrane (stratum corneum and viable epidermis) and assessing which drug and or formulations are able to permeate with or without physical or chemical permeation enhancers. The second step, using candidates that permeate or retain in the epidermal membrane, uses the human dermal membrane. Those candidates that permeate the dermis can be considered for systemic delivery, while those not permeating the dermis are considered for local delivery.

Example 8

FIG. 15 of Example 8 illustrates the types of formulation libraries that can be obtained and included in the permeation and retention screening. As shown in FIG. 14, underlined text means the formulation is stable and it will be included in the permeation and retention screening, italicized text indicates the formulation may possibly be included but may need to change the formulation, and plain text indicates the formulation will not be included due to incompatibilities between ingredients.

Example 9

Figure 16:
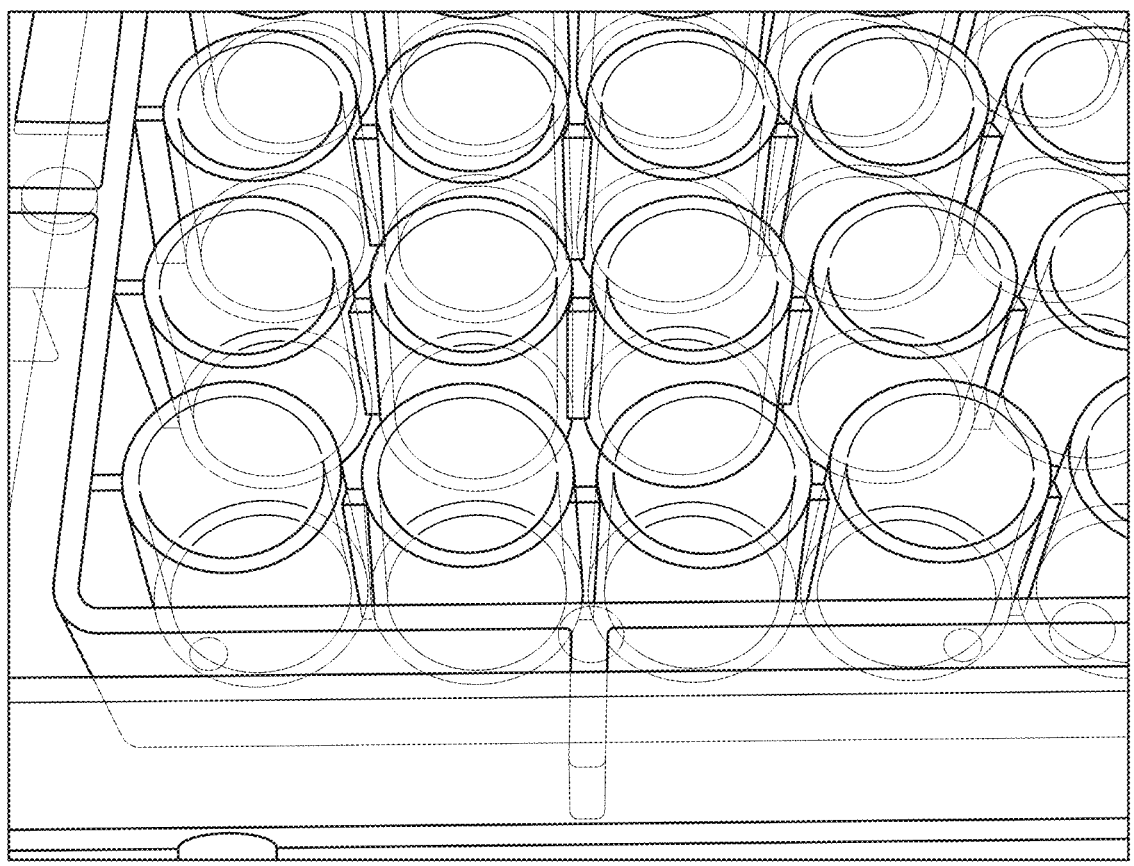
FIG. 16 illustrates a photograph wells suitable for use in embodiments disclosed herein.

FIG. 16 illustrates a photograph wells suitable for use in embodiments disclosed herein. The embodiment disclosed in FIG. 16 includes wells with rims that are essentially rectangular. In addition, each well has walls that are separate from the walls of other wells, and the wells are connected below the rim. Each well is elevated above the plate plane.

Example 10

A permeation study was done using the 96-well plates screening method over a course of 24 hours. Doxycycline at different concentrations was used as a model drug. After 24 hours, the receptor fluid was removed, and the plates were disassembled. The mass spec pen (described by Zhang et al. and Sans et al.) was used to measure the amount of doxycycline on the top layers of the skin (epidermis side) and on the bottom layers of the skin (dermis side) by flipping the skin upside down (26, 27). Changes in permeation were detected for different concentrations of doxycycline applied.

REFERENCES

The contents of the following references are incorporated by reference herein:
1. Franz T J. Percutaneous absorption. On the relevance of in vitro data. Journal of Investigative Dermatology. 1975; 64(3):190-5.
2. Franz T J. The finite dose technique as a valid in vitro model for the study of percutaneous absorption in man. Skin-Drug Application and Evaluation of Environmental Hazards. 7: Karger Publishers; 1978. p. 58-68.

3. Karande P, Mitragotri S. High throughput screening of transdermal formulations. Pharmaceutical research. 2002 May 1; 19(5):655-60.
4. Avdeef A, Nielsen P E, Du C M, inventors; pION Inc, assignee. Method and apparatus for improving in vitro measurement of membrane permeability of chemical compounds. U.S. Pat. No. 7,022,528. Apr. 4, 2006.
5. Sinkó B, Garrigues T M, Balogh G T, Nagy Z K, Tsinman O, Avdeef A, Takács-Novák K. Skin—PAMPA: A new method for fast prediction of skin penetration. European Journal of Pharmaceutical Sciences. 2012 Apr. 11; 45(5): 698-707.
6. Rossetti FbC, Depieri LvV, Bentley M VrLB. Confocal laser scanning microscopy as a tool for the investigation of skin drug delivery systems and diagnosis of skin disorders. Confocal Laser Microscopy-Principles and Applications in Medicine, Biology, and the Food Sciences: InTech; 2013.
7. Alvarez-Román R, Naik A, Kalia Y N, Guy R H, Fessi H. Skin penetration and distribution of polymeric nanoparticles. J Control Release. 2004; 99(1):53-62.
8. Alvarez-Roman R, Naik A, Kalia Y, Fessi H, Guy R H. Visualization of skin penetration using confocal laser scanning microscopy. Eur J Pharm Biopharm. 2004; 58(2):301-16.
9. Tsai T H, Jee S H, Dong C Y, Lin S J. Multiphoton microscopy in dermatological imaging. J Dermatol Sci. 2009; 56(1):1-8
10. David W. Piston T J F, Michael W. Davidson. Multiphoton Microscopy: Fundamentals and Applications in Multiphoton Excitation Microscopy 2017 [updated 2017; cited 2017. Available from: https://www.microscopyu.com/techniques/multi-photon/multiphoton-microscopy.
11. Lucassen G W, Hendriks R F. 13 Two-Photon Microscopy and Confocal Laser Scanning Microscopy of In Vivo Skin. Bioengineering of the skin: skin imaging and analysis. 2006:177.
12. Kirejev V, Guldbrand S, Borglin J, Simonsson C, Ericson M. Multiphoton microscopy. a powerful tool in skin research and topical drug delivery science. Journal of drug delivery science and technology. 2012; 22(3):250-9.
13. Balu, M., Tromberg, B. J., 2015. Multiphoton microscopy for non-invasive optical biopsy of human skin. Multiphoton microscopy—instrument optic non-invaziv de evaluare a pieli. Roman. J. Clin. Exp. Dermatol. 2 (3).
14. Food and Drug Administration (FDA) H. Draft Guidance for Industry on Topical Dermatological Drug Product N DAs and ANDAs—In Vivo Bioavailability, Bioequivalence, In Vitro Release and Associated Studies. In: (CDER) CfDEaR, editor. June 1998.
15. Roberts M S, Dancik Y, Prow T W, Thorling C A, Lin L L, Grice J E, et al. Non-invasive imaging of skin physiology and percutaneous penetration using fluorescence spectral and lifetime imaging with multiphoton and confocal microscopy. Eur J Pharm Biopharm. 2011; 77(3): 469-88.
16. Campagnola P. Second harmonic generation imaging microscopy: applications to diseases diagnostics. Anal Chem. 2011; 83(9):3224-31.
17. Ashtikar M, Matthäus C, Schmitt M, Krafft C, Fahr A, Popp J. Non-invasive depth profile imaging of the stratum corneum using confocal Raman microscopy: first insights into the method. Eur J Pharm Sci. 2013; 50(5):601-8.
18. Franzen L, Selzer D, Fluhr J W, Schaefer U F, Windbergs M. Towards drug quantification in human skin with confocal Raman microscopy. Eur J Pharm Biopharm. 2013; 84(2):437-44.
19. Ascencio S M, Choe C, Meinke M C, Muller R H, Maksimov G V, Wigger-Alberti W, et al. Confocal Raman microscopy and multivariate statistical analysis for determination of different penetration abilities of caffeine and propylene glycol applied simultaneously in a mixture on porcine skin ex vivo. Eur J Pharm Biopharm. 2016; 104:51-8.
20. U.S. Pat. No. 5,490,415
21. U.S. Pat. No. 6,043,027
22. U.S. Pat. No. 7,022,528
23. U.S. Pat. No. 8,277,762
24. U.S. Pat. Pub. 2007/0183936
25. PCT Pat. Pub. WO 02/06518 A1
26. Zhang J, Rector J, Lin J Q, Young J H, Sans M, Katta N, Giese N, Yu W, Nagi C, Suliburk J, Liu J. Nondestructive tissue analysis for ex vivo and in vivo cancer diagnosis using a handheld mass spectrometry system. Science translational medicine. 2017 Sep. 6; 9(406):eaan3968.
27. Sans M, Zhang J, Lin J Q, Feider C L, Giese N, Breen M T, Sebastian K, Liu J, Sood A K, Eberlin L S. Performance of the MasSpec Pen for Rapid Diagnosis of Ovarian Cancer. Clinical chemistry. 2019 May 1; 65(5): 674-83.

The invention claimed is:

1. A method of analyzing membrane retention and permeation, the method comprising:
securing a biological barrier between a first plurality of wells and a second plurality of wells;
contacting the biological barrier with a compound, wherein:
the compound is initially contained in the first plurality of wells;
the compound is in contact with the biological barrier for a period of time; and
the compound comprises an optically detectable compound and a therapeutic agent;
removing the biological barrier from between the first plurality of wells and the second plurality of wells;
analyzing the biological barrier to determine an amount of the optically detectable compound retained in the biological barrier, wherein:
the biological barrier comprises a dermal or epidermal membrane;
analyzing the biological barrier to determine the amount of the optically detectable compound retained in the biological barrier comprises an optical analysis of the biological barrier; and
the optical analysis comprises:
directing an excitation light toward the biological barrier; and
measuring an emitted light from the biological barrier.

2. The method of claim 1 wherein the optical analysis comprises multi-photon microscopy.

3. The method of claim 1 wherein the optical analysis comprises two-photon microscopy.

4. The method of claim 1 wherein the optical analysis comprises Raman spectroscopy.

5. The method of claim 1 wherein the emitted light is fluorescence emitted from the optically detectable compound.

6. The method of claim 1 wherein the period of time is at least one hour.

7. The method of claim 1 wherein the period of time is at least eight hours.

8. The method of claim 1 wherein the first plurality of wells and the second plurality of wells each comprise at least 96 wells.

9. The method of claim 1, wherein:
the first plurality of wells is configured in a first planar array;
the second plurality of wells is configured in a second planar array; and
the method further comprising clamping the first planar array to the second planar array.

* * * * *